US008451975B2

(12) United States Patent
Tada

(10) Patent No.: US 8,451,975 B2
(45) Date of Patent: May 28, 2013

(54) RADIOGRAPHIC SYSTEM, RADIOGRAPHIC METHOD AND COMPUTER READABLE MEDIUM

(75) Inventor: Takuji Tada, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 209 days.

(21) Appl. No.: 13/035,551

(22) Filed: Feb. 25, 2011

(65) Prior Publication Data

US 2011/0243305 A1      Oct. 6, 2011

(30) Foreign Application Priority Data

Mar. 30, 2010  (JP) ............................... P2010-079915
Sep. 30, 2010  (JP) ............................... P2010-223290
Jan. 19, 2011  (JP) ............................... P2011-009176

(51) Int. Cl.
*G01D 18/00*        (2006.01)
*G01N 23/201*       (2006.01)

(52) U.S. Cl.
USPC ........................................... 378/87; 378/207

(58) Field of Classification Search
USPC ........................................ 378/87, 98.8, 207
See application file for complete search history.

(56) References Cited

U.S. PATENT DOCUMENTS

| 7,180,979 B2 | 2/2007 | Momose |
| 7,889,838 B2 | 2/2011 | David et al. |
| 2009/0110144 A1 | 4/2009 | Takahashi et al. |
| 2010/0119041 A1* | 5/2010 | Ohara .............................. 378/87 |

FOREIGN PATENT DOCUMENTS

| JP | 2008-545981 T | 12/2008 |
| JP | 2009-133823 A | 6/2009 |
| WO | WO 2004/058070 A1 | 7/2004 |
| WO | WO 2006/131235 A1 | 12/2006 |

OTHER PUBLICATIONS

Hector Canabal, et al., "Improved phase-shifting method for automatic processing of moiré deflectograms", Applied Optics, Sep. 1998, vol. 37, No. 26, pp. 6227-6233.

\* cited by examiner

*Primary Examiner* — Irakli Kiknadze
(74) *Attorney, Agent, or Firm* — McGinn IP Law Group, PLLC

(57) ABSTRACT

A radiographic system which detects a radiation image transmitted through a subject with a radiation image detector and generates a phase contrast image of the subject, includes: a calculation section that calculates a distribution of refraction angles of radiation incident on the radiation image detector and generates the phase contrast image on the basis of the distribution of refraction angles; and a storage section that stores a correction coefficient of each pixel for making sensitivities of pixels equal. The calculation section performs sensitivity correction on a refraction angle of radiation incident on each pixel of the radiation image detector, which is calculated by imaging the subject, using the correction coefficient of the pixel stored in the storage section and generates the phase contrast image of the subject on the basis of the distribution of corrected refraction angles.

19 Claims, 19 Drawing Sheets

RADIOGRAPHIC SYSTEM, RADIOGRAPHIC METHOD AND COMPUTER READABLE MEDIUM

CROSS-REFERENCE TO RELATED APPLICATIONS

This application is based on and claims priority under 35 USC 119 from Japanese Patent Application Nos. 2010-079915 filed on Mar. 30, 2010, 2010-223290 filed on Sep. 30, 2010 and 2011-009176 filed on Jan. 19, 2011; the entire contents of which are incorporated herein by reference.

BACKGROUND

1. Technical Field

The present invention relates to a radiographic system, a radiographic method of imaging a subject using radiation, such as X-rays and a computer readable medium.

2. Related Art

X-rays are used as a probe for seeing through a subject since the X-rays are attenuated depending on the atomic number of an element, which forms a material, and the density and thickness of the material. Imaging using X-rays has been widespread in fields such as medical diagnosis and non-destructive inspection.

In a general X-ray imaging system, a subject is disposed between an X-ray source which emits X-rays and an X-ray image detector which detects X-rays and a transmission image of the subject is captured. In this case, each X-ray emitted from the X-ray source toward the X-ray image detector is attenuated (absorbed) by the amount corresponding to the difference in properties (atomic number, density, and thickness) of materials present on the path to the X-ray image detector and is then incident on each pixel of the X-ray image detector. As a result, an X-ray absorption image of the subject is detected by the X-ray image detector and imaged. As the X-ray image detector, not only the combination of an X-ray intensifying screen and a film or photostimulable phosphor but also a flat panel detector (FPD) using a semiconductor circuit is widely used.

However, since the X-ray absorption ability of the material decreases as the atomic number of the element constituting the material decreases, there is a problem in that the contrast of an image sufficient as an X-ray absorption image is not obtained in a soft biological tissue or a soft material. For example, most components of a cartilaginous portion, which forms the joint of a human body, and joint fluid around the cartilaginous portion are water. Accordingly, since the difference between their X-ray absorption amounts is small, it is difficult to acquire the intensity difference.

In recent years, in order to solve such a problem, X-ray phase imaging has been actively studied which is for acquiring an image (hereinafter, referred to as a phase contrast image) based on a phase change (angle change) of X-rays by a subject instead of an intensity change of X-rays by a subject. Generally, it is known that interaction between the phases of X-rays is stronger than interaction between the intensities of X-rays when X-rays are incident on a material. For this reason, in the X-ray phase imaging using a phase difference, an image with high contrast can be acquired even in the case of a weak absorption material with a low X-ray absorption ability. As one of such an X-ray phase imaging system, an X-ray imaging system using an X-ray Talbot interferometer which includes two transmissive diffraction gratings (phase grating or absorption grating) and an X-ray image detector has been recently proposed (for example, see Patent Document 1 (WO-A-2004/058070)).

The X-ray Talbot interferometer is formed by disposing a first diffraction grating (phase grating or absorption grating) behind a subject, disposing a second diffraction grating (absorption grating) at the downstream side by the specific distance (Talbot interference distance) determined by the grating pitch of the first diffraction grating and the X-ray wavelength, and disposing an X-ray image detector therebehind. The Talbot interference distance is a distance in which X-rays transmitted through the first diffraction grating form a self-image by the Talbot interference effect, and this self-image is modulated by interaction (phase change) of the subject, which is disposed between the X-ray source and the first diffraction grating, and X-rays.

In the X-ray Talbot interferometer, moiré fringes generated by superposition of the self-image of the first diffraction grating and the second diffraction grating are detected, and the phase information of the subject is acquired by analyzing a change of the moiré fringes by the subject. As an example of the method of analyzing moiré fringes, a fringe scanning method is proposed. According to the fringe scanning method, imaging is performed a plural number of times while performing translational movement of the second diffraction grating with respect to the first diffraction grating by a scanning pitch, which is obtained by equal division of the grating pitch, in a direction almost parallel to the surface of the first diffraction grating and in a direction almost perpendicular to the lattice direction (strip direction) of the first diffraction grating, and the angle distribution (phase-shifted differential image) of X-rays refracted at the subject is acquired from a change in the signal value of each pixel obtained by the X-ray image detector. On the basis of this angle distribution, a phase contrast image of the subject can be acquired.

In addition, phase imaging based on image capturing using a Talbot interferometer has been proposed, before the X-ray phase imaging, for visible light (for example, He—Ne laser) which is highly coherent like X-rays (for example, refer to Non-patent Document 1 (Hector Canabal, et al., "Improved phase-shifting method for automatic processing of moiré deflectograms", APPLIED OPTICS, September, 1998, Vol. 37, No. 26, p. 6227-6233)).

In the phase imaging described above, the signal value of each pixel of the X-ray image detector obtained by performing translation movement of the second diffraction grating by a predetermined scanning pitch is given by the following expression (1) according to Patent Document 1.

[Expression 1]

$$I(x, y) = A_0 + \sum_{k=1} A_k \cos\left[\frac{2\pi k}{d}\{\delta(x, y) + Z\varphi(x, y) + \xi\}\right] \quad (1)$$

Here, $A_k$ (k=0, 1, ...) is a constant determined by the shape of a diffraction grating, d is a period of a grid pattern of the second diffraction grating, $\delta(x, y)$ is an offset value occurring due to distortion, manufacturing error, or arrangement error of a diffraction grating, Z is a distance between the first and second diffraction gratings, $\varphi(x, y)$ is a refraction angle of X-rays by the subject, and $\xi$ is the amount of translation movement of the second diffraction grating.

A self-image of the first diffraction grating is displaced by the amount corresponding to the refraction angle $\delta$ due to refraction of X-rays at the subject. Here, the refraction angle φ(x, y) is expressed by the following expression (2) using the X-ray wavelength λ and the phase shift distribution Φ(x, y) of the subject.

[Expression 2]

$$\varphi = \frac{\lambda}{2\pi}\frac{\partial \Phi(x,y)}{\partial x} \quad (2)$$

Thus, the amount of displacement of a self-image of the first diffraction grating, which is caused by refraction of X-rays at the subject, is associated with the phase shift distribution Φ(x, y) of the subject. Assuming that the amount of displacement is Δ, the amount of displacement Δ is associated with the amount of phase shift ψ of an intensity-modulated signal of each pixel (the amount of phase shift of an intensity-modulated signal of each pixel when there is a subject and when there is no subject) of the image detector, which is obtained by scanning the second diffraction grating, as expressed by the following expression (3).

[Expression 3]

$$\psi(x,y) = \frac{2\pi}{d}\Delta = \frac{2\pi}{d}Z\varphi(x,y) \quad (3)$$

In addition, when a subject is spherical, φ(x, y) in the edge section is given by the following expression (4).

[Expression 4]

$$\phi(x,y) \propto \sqrt{1/D} \times \Delta n \quad (4)$$

Here, D is a width of each pixel of the image detector in the scanning direction of the second diffraction grating, and Δn is a refractive index difference between a subject and a medium around the subject.

From expressions (1) to (4), calculating the refraction angle φ from the amount of phase shift ψ acquired from the intensity-modulated signal of each pixel of the image detector is influenced by the period d of a grid pattern of the second diffraction grating, the distance Z between the first and second diffraction gratings, and the width D of each pixel of the X-ray image detector.

Regarding the period d of the grid pattern of the second diffraction grating, distortion or a manufacturing error of the second diffraction grating causes an error in the period d of the grid pattern and the refraction angle φ is changed by the error of the period d.

In addition, regarding the distance Z between the first and second diffraction gratings, the distance between the first and second diffraction gratings along X-rays differs with each section in the case where X-rays emitted from the X-ray source are cone beams and both the first and second diffraction gratings are formed in the flat plate shapes. As shown in FIG. 21, for example, when an X-ray is transmitted through middle sections of first and second diffraction gratings G1 and G2 in a direction approximately perpendicular to these diffraction gratings, the distance between the first and second diffraction gratings along the X-ray, that is, the path length $Z_1$ of the X-ray becomes shortest. On the other hand, in peripheral sections of the first and second diffraction gratings, an X-ray is transmitted through the first and second diffraction gratings in an inclined state, and the path length $Z_2$ of the X-ray increases toward the periphery. Due to this change of the path length Z, the refraction angle φ also changes.

In addition, regarding the width D of each pixel of the X-ray image detector, in the case where X-rays emitted from the X-ray source are cone beams, the angle of incidence of an X-ray on each pixel of the X-ray image detector differs with each section of the X-ray image detector because the X-ray image detector is typically flat. As shown in FIG. 22, for example, when an X-ray is incident on a pixel 40 in a middle section of an X-ray image detector 30 so as to be approximately perpendicular to the pixel 40 (when the angle of incidence of an X-ray is large), an X-ray is incident on the pixel 40 in a peripheral section so as to be inclined according to the movement toward the periphery (the angle of incidence of the X-ray is reduced). Therefore, the effective width of each pixel 40, that is, the projection width of each pixel 40 when each pixel is projected vertically to the plane perpendicular to the middle line of X-rays incident on the pixel differs with each section of the X-ray image detector. If the effective widths of pixels are different, the signal values of the pixels are different even if the phase shifts of incident X-rays are the same.

In Patent Document 1, the above-described error factors are not taken into consideration at all. For this reason, original contrast for acquisition is not acquired or unnecessary contrast is acquired in a phase contrast image created on the basis of the refraction angle distribution.

SUMMARY

An illustrative aspect of the invention is to improve the precision of phase imaging in a radiographic system and a radiographic method of performing phase imaging of a subject.

According to an aspect of the invention, a radiographic system which detects a radiation image transmitted through a subject with a radiation image detector and generates a phase contrast image of the subject includes: a calculation section which calculates the distribution of refraction angles of radiation incident on the radiation image detector and generates a phase contrast image on the basis of the distribution of refraction angles; and a storage section which stores a correction coefficient of each pixel for making sensitivities of pixels equal, the correction coefficient being calculated on the basis of a refraction angle of radiation incident on each pixel of the radiation image detector, which is calculated by the calculation section by imaging a phantom that gives a known refraction angle to radiation transmitted through the phantom, and a refraction angle given to radiation by the phantom, wherein the calculation section performs sensitivity correction on a refraction angle of radiation incident on each pixel of the radiation image detector, which is calculated by imaging the subject, using the correction coefficient of the pixel stored in the storage section and generates a phase contrast image of the subject on the basis of the distribution of corrected refraction angles.

According to another aspect of the invention, a radiographic method of detecting a radiation image transmitted through a subject with a radiation image detector and generating a phase contrast image of the subject includes: calculating a correction coefficient of each pixel for making sensitivities of pixels equal on the basis of a refraction angle of radiation incident on each pixel of the radiation image detector, which is calculated by imaging a phantom that gives a known refraction angle to radiation transmitted through the phantom, and a refraction angle given to radiation by the phantom; and performing sensitivity correction on a refraction angle of radiation incident on each pixel of the radiation image detector, which is calculated by imaging the subject, using the correction coefficient of the pixel and generating a phase contrast image of the subject on the basis of the distribution of corrected refraction angles.

According to the aspects of the invention, it is possible to correct a plurality of imaging errors, which is caused by a plurality of error factors included in an imaging system, in phase imaging. In addition, since a plurality of imaging errors caused by a plurality of error factors can be corrected simultaneously instead of correcting an imaging error caused by each error factor separately, the correction can be performed easily and precisely. Accordingly, the precision of phase imaging can be improved.

DETAILED DESCRIPTION

Figure 1:
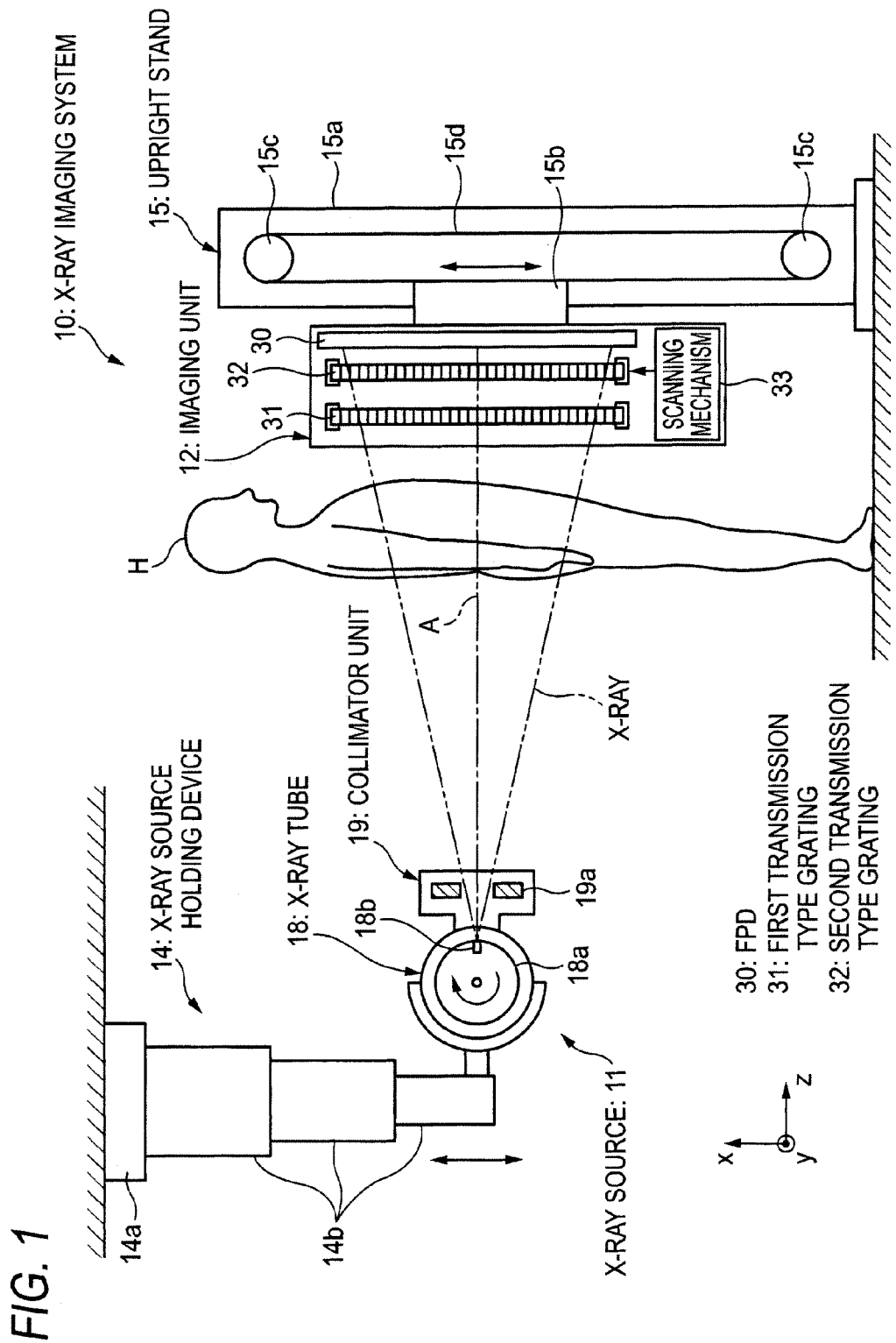
FIG. 1 is a schematic view showing the configuration of an example of a radiographic system for explaining an embodiment of the invention.
Figure 2:
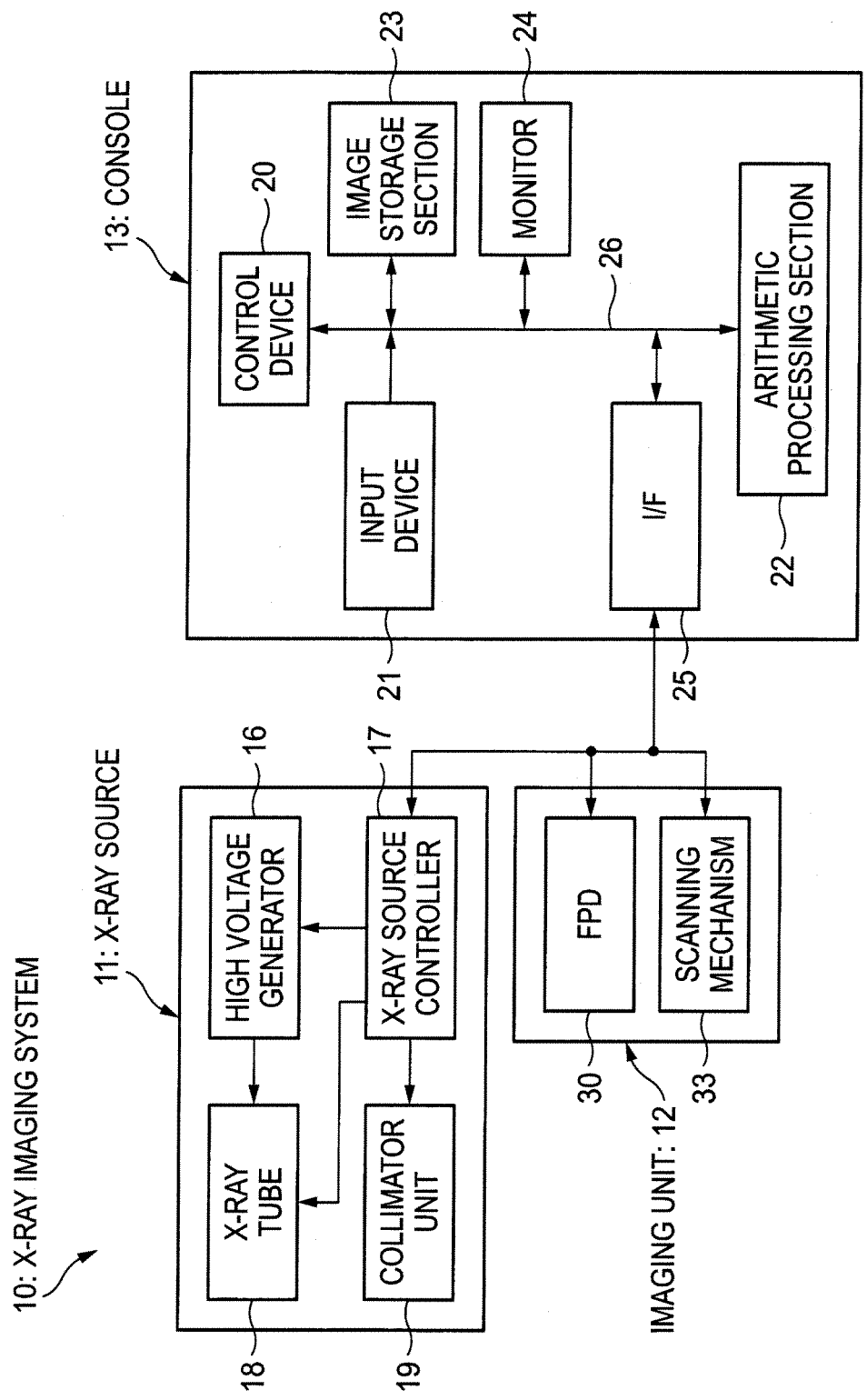
FIG. 2 is a block diagram showing the control configuration of the radiographic system shown in FIG. 1.

An X-ray imaging system 10 shown in FIGS. 1 and 2 is an X-ray diagnostic apparatus which images a subject (patient) H in a standing state and mainly includes: an X-ray source 11 which emits X-rays to the subject H; an imaging unit 12 which is disposed opposite the X-ray source 11 and which detects X-rays transmitted through the subject H from the X-ray source 11 and generates the image data; and a console 13 which controls an exposure operation of the X-ray source 11 or an imaging operation of the imaging unit 12 on the basis of an operation of the operator and which generates a phase contrast image by arithmetic processing of the image data acquired by the imaging unit 12.

The X-ray source 11 is held by an X-ray source holding device 14 suspended from the ceiling so as to freely move in a vertical direction (x direction). The imaging unit 12 is held by an upright stand 15 installed on the floor so as to freely move in the vertical direction.

The X-ray source 11 includes an X-ray tube 18, which generates X-rays by a high voltage applied from a high voltage generator 16 on the basis of control of an X-ray source controller 17, and a collimator unit 19 having a movable collimator 19a that restricts an exposure field on the basis of control of the X-ray source controller 17 so that X-rays, which are not emitted to the inspection region of the subject H, among the X-rays emitted from the X-ray tube 18 are blocked. The X-ray tube 18 is of an anode rotation type, and generates X-rays by emitting electron beams from a filament (not shown) as an electron emission source (negative electrode) and making the electron beams collide with a rotating anode 18a which rotates at a predetermined speed. A portion of the rotating anode 18a colliding with electron beams becomes an X-ray focal point 18b.

The X-ray source holding device 14 includes a carriage 14a, which is formed to freely rotate in a horizontal direction (z direction) by a ceiling rail (not shown) installed on the ceiling, and a plurality of columns 14b connected to carriage 14a in the vertical direction. A motor (not shown) which changes the position of the X-ray source 11 in the vertical direction by expanding or contracting the columns 14b is provided in the carriage 14a.

The upright stand 15 is fixed to a main body 15a installed on the floor such that a holding section 15b, which holds the imaging unit 12, freely moves in the vertical direction. The holding section 15b is connected to an endless belt 15d hanging between two pulleys 15c, which are separated from each other in the vertical direction, and is driven by a motor (not shown) that rotates the pulleys 15c. Driving of this motor is controlled by a control device 20 of the console 13, which will be described later, on the basis of a setting operation of an operator.

In addition, a position sensor (not shown), such as a potentiometer which detects the position of the imaging unit 12 in the vertical direction by measuring the amount of movement of the pulleys 15c or the endless belt 15d, is provided in the upright stand 15. The detection value of the position sensor is supplied to the X-ray source holding device 14 through a cable or the like. The X-ray source holding device 14 moves the X-ray source 11 so as to follow the vertical movement of the imaging unit 12 by expanding or contracting the columns 14b on the basis of the supplied detection value.

The control device 20 including a CPU, a ROM, a RAM, and the like is provided in the console 13. An input device 21 which is used when an operator inputs an imaging instruction or the instruction content, an arithmetic processing section 22 which generates an X-ray image by performing arithmetic processing of image data acquired by the imaging unit 12, a storage section 23 which stores an X-ray image, a monitor 24 which displays an X-ray image or the like, and an interface (UF) 25 connected to each section of the X-ray imaging system 10 are connected to the control device 20 through a bus 26. Various kinds of processing programs and a control program for controlling each section connected through the bus 26 are stored in the ROM of the control device 20, and the CPU performs overall control of an operation of each section by cooperation of the control program and various processing programs in order to perform X-ray imaging.

As the input device 21, for example, a switch, a touch panel, a mouse, and a keyboard may be used. X-ray imaging conditions, such as an X-ray tube voltage or an X-ray exposure time, an imaging timing, and the like are input by operation of the input device 21. The monitor 24 is formed by a liquid crystal display or the like and displays an X-ray image or characters, such as X-ray imaging conditions, by control of the control device 20.

A flat panel detector (FPD) 30 formed by a semiconductor circuit and first and second transmission type gratings 31 and 32 for detecting a phase change (angle change) of X-rays by the subject H and performing phase imaging are provided in the imaging unit 12. The FPD 30 is disposed such that the detection surface is perpendicular to the optical axis A of X-rays emitted from the X-ray source 11. The first and second transmission type gratings 31 and 32 are disposed between the FPD 30 and the X-ray source 11 and will be described in detail later. In addition, a scanning mechanism 33 which changes the relative position of the second transmission type grating 32 with respect to the first transmission type grating 31 by performing translational movement of the second transmission type grating 32 in the vertical direction is provided in the imaging unit 12. For example, the scanning mechanism 33 is formed by an actuator, such as a piezoelectric element.

Figure 3:
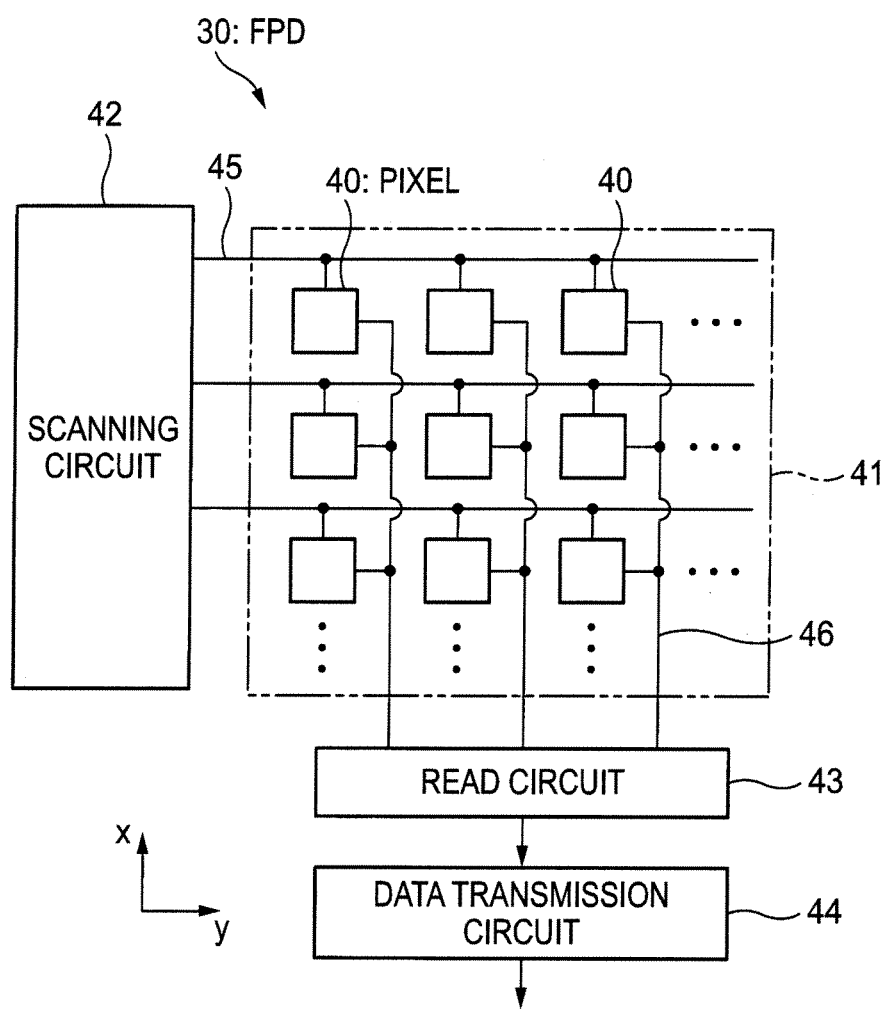
FIG. 3 is a schematic view showing the configuration of a radiation image detector.

As shown in FIG. 3, the FPD 30 includes: an image receiving section 41 in which a plurality of pixels 40, which converts X-rays into electric charges and stores the electric charges, is arrayed on an active matrix substrate in the xy direction in a two-dimensional manner; a scanning circuit 42 which controls a read timing of electric charges from the image receiving section 41; a read circuit 43 which reads an electric charge stored in each pixel 40 and converts the electric charge into image data and stores it; and a data transmission circuit 44 which transmits the image data to the arithmetic processing section 22 through the I/F 25 of the console 13. In addition, the scanning circuit 42 and each pixel 40 are connected to each row by a scanning line 45, and the read circuit 43 and each pixel 40 are connected to each column by a signal line 46.

Each pixel 40 may be formed as a direct conversion type element in which a conversion layer (not shown) formed of amorphous selenium or the like directly converts X-rays into electric charges and the converted electric charges are stored in a capacitor (not shown) connected to an electrode below the conversion layer. A TFT switch (not shown) is connected to each pixel 40, and a gate electrode, a source electrode, and a drain electrode of the TFT switch are connected to the scanning line 45, the capacitor, and the signal line 46, respectively. When a TFT switch is turned ON by a driving pulse from the scanning circuit 42, electric charges stored in the capacitor are read to the signal line 46.

In addition, each pixel 40 may also be formed as an indirect conversion type X-ray detection element in which a scintillator (not shown) formed of gadolinium oxide ($Gd_2O_3$), cesium iodide (CsI), or the like converts X-rays into visible light first, the converted visible light is converted into electric charges by a photodiode (not shown), and the electric charges are stored. In addition, the X-ray image detector is not limited to the FPD based on the TFT panel, and it is also possible to use various kinds of X-ray image detectors based on solid-state imaging devices, such as a CCD sensor and a CMOS sensor.

The read circuit 43 is formed by an integration amplifier circuit, an A/D converter, a correction circuit, and an image memory (not shown). The integration amplifier circuit integrates an electric charge output from each pixel 40 through the signal line 46, converts it into a voltage signal (image signal), and inputs it into the A/D converter. The A/D converter converts the input image signal into digital image data and inputs it to the correction circuit. The correction circuit performs offset correction, gain correction, and linearity correction for the image data and stores the image data after correction in the image memory. In addition, correction of the amount of exposure of X-rays or exposure distribution (so-called shading), correction of pattern noise (for example, a leak signal of a TFT switch) depending on the control conditions (driving frequency or read period) of the FPD 30, and the like may be included as correction processing of the correction circuit.

Figure 4:
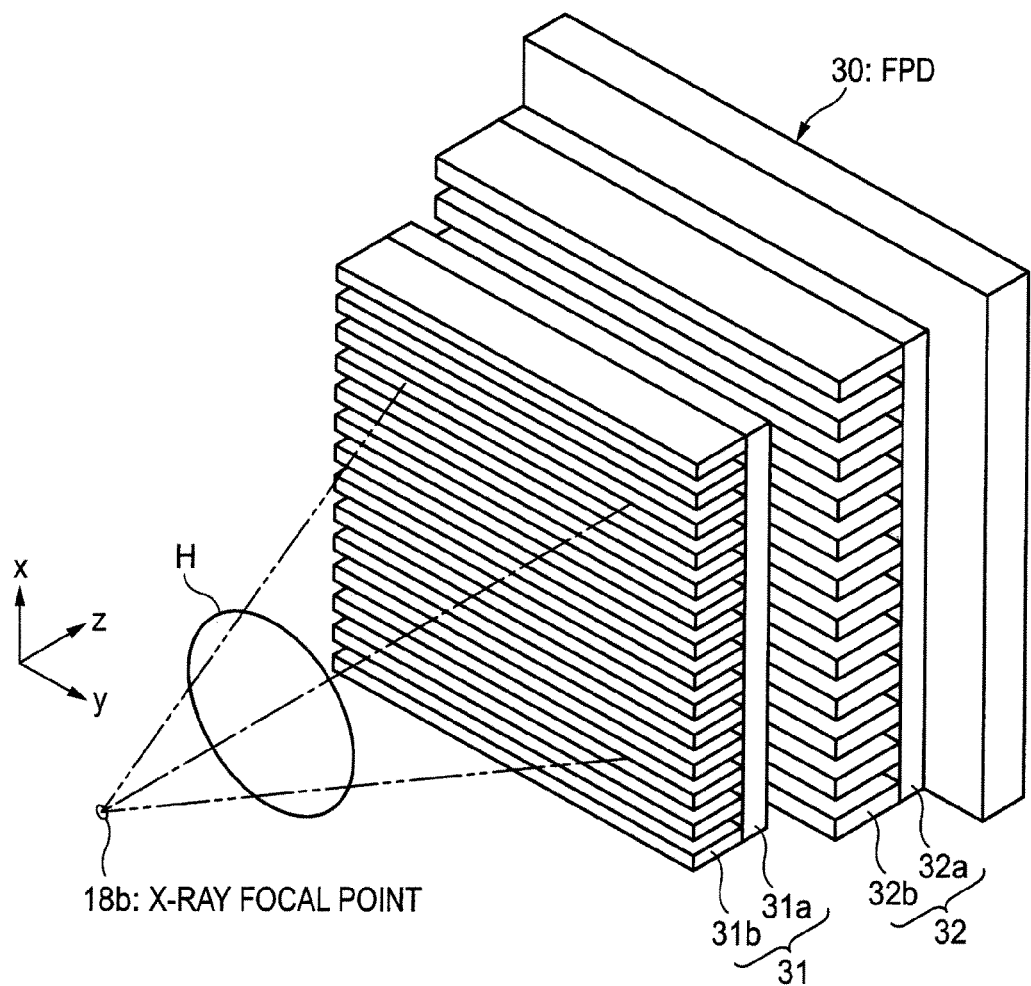
FIG. 4 is a perspective view showing the configurations of first and second transmission type gratings.
Figure 5:
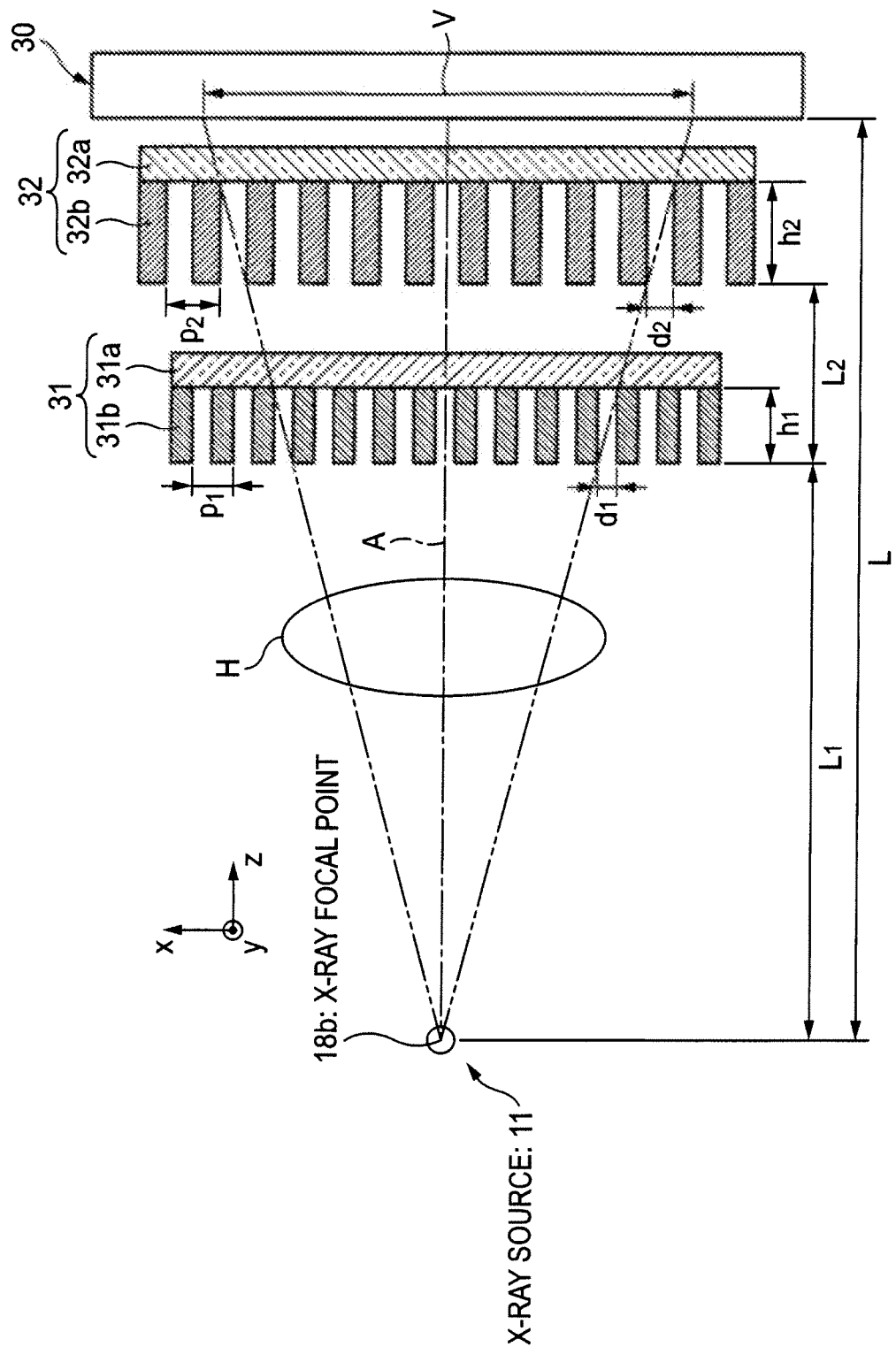
FIG. 5 is a side view showing the configurations of first and second transmission type gratings.

As shown in FIGS. 4 and 5, the first transmission type grating 31 is formed by a substrate 31a and a plurality of X-ray blocking sections 31b arrayed on the substrate 31a. Similarly, the second transmission type grating 32 is formed by a substrate 32a and a plurality of X-ray blocking sections 32b arrayed on the substrate 32a. Both the substrates 31a and 31b are formed of a radiolucent member, such as glass through which X-rays are transmitted.

Both the X-ray blocking sections 31b and 32b are linear members extending in one direction (in the example shown in the drawings, a y direction perpendicular to x and z directions) within the plane perpendicular to the optical axis A of X-rays emitted from the X-ray source 11. As materials of the X-ray blocking sections 31b and 32b, materials with excellent X-ray absorption properties are preferable. For example, metal, such as gold and platinum, is preferably used. The X-ray blocking sections 31b and 32b may be formed using a metal plating method or a vapor deposition method.

The X-ray blocking sections 31b are arrayed at fixed pitches $p_1$ in a direction (in the example shown in the drawings, the x direction) perpendicular to the above-mentioned one direction and at predetermined distances $d_1$ therebetween within the plane perpendicular to the optical axis A of X-rays. Similarly, the X-ray blocking sections 32b are arrayed at fixed pitches $p_2$ in a direction (in the example shown in the drawings, the x direction) perpendicular to the above-mentioned one direction and at predetermined distances $d_2$ therebetween within the plane perpendicular to the optical axis A of X-rays. Since the first and second transmission type gratings 31 and 32 are not for giving the phase difference to incident X-rays but for giving the intensity difference, they are called absorption type gratings or amplitude type gratings especially in transmission type gratings. In addition, a slit section (regions of the distances $d_1$ and $d_2$) may not be filled or may be filled with a material which absorbs a small amount of X-rays, such as polymer or light metal.

The first and second transmission type gratings 31 and 32 are formed to geometrically project X-rays transmitted through the slit section irrespective of the Talbot interference effect. Specifically, the first and second transmission type gratings 31 and 32 are formed to allow most X-rays included in emitted X-rays to be transmitted therethrough while maintaining the straightness without diffracting them in a slit section by setting the distances $d_1$ and $d_2$ to sufficiently larger values than the peak wavelength of X-rays emitted from the X-ray source 11. For example, when a tube voltage is set to 50 kV using tungsten as the rotating anode 18a, the peak wavelength of X-rays is about 0.4 Å. In this case, if the distances $d_1$ and $d_2$ are set to about 1 to 10 μm, most X-rays are geometrically projected without being diffracted at the slit section.

X-rays emitted from the X-ray source 11 are not parallel beams but cone beams having the X-ray focal point 18b as an emission point. Accordingly, a projection image (hereinafter, this projection image is called a G1 image) obtained when the X-rays emitted from the X-ray source 11 are projected after passing through the first transmission type grating 31 expands in proportion to the distance from the X-ray focal point 18b. The grating pitch $p_2$ of the second transmission type grating 32 is determined such that the slit section almost matches a periodic pattern of a bright portion of a G1 image at the position of the second transmission type grating 32. That is, assuming that the distance from the X-ray focal point 18b to the first transmission type grating 31 is $L_1$ and the distance from the first transmission type grating 31 to the second transmission type grating 32 is $L_2$, the grating pitch $p_2$ is determined so as to satisfy the relationships of the following expressions (5).

[Expression 5]

$$p_2 = \frac{L_1 + L_2}{L_1} p_1 \qquad (5)$$

In the Talbot interferometer, the distance $L_2$ from the first transmission type grating 31 to the second transmission type grating 32 is restricted by the Talbot interference distance determined by the grating pitch of the first diffraction grating and the X-ray wavelength. In the imaging unit 12 of the X-ray imaging system 10, however, the first transmission type grating 31 has a structure in which incident X-rays are projected without being diffracted and a G1 image of the first transmission type grating 31 is similarly obtained at all positions behind the first transmission type grating 31. Accordingly, the distance $L_2$ can be set regardless of the Talbot interference distance.

Although the imaging unit 12 is not a constituent component of the Talbot interferometer as described above, a Talbot interference distance Z when it is assumed that X-rays are diffracted at the first transmission type grating 31 is expressed by the following expression (6) using the grating pitch $p_1$ of the first transmission type grating 31, the grating pitch $p_2$ of the second transmission type grating 32, the X-ray wavelength (peak wavelength) λ, and the positive integer m.

[Expression 6]

$$Z = m \frac{p_1 p_2}{\lambda} \qquad (6)$$

Expression (6) is an expression indicating the Talbot interference distance when X-rays emitted from the X-ray source 11 are cone beams, and is known from "Atsushi Momose, et al., Japanese Journal of Applied Physics, Vol. 47, and No. 10, October, 2008, pp. 8077".

In the X-ray imaging system 10, the distance $L_2$ is set to a value shorter than the minimum Talbot interference distance Z when m is 1 in order to make the imaging unit 12 thin. That is, the distance $L_2$ is set as a value in a range which satisfies the following expression (7).

[Expression 7]

$$L_2 < \frac{p_1 p_2}{\lambda} \qquad (7)$$

In addition, the Talbot interference distance Z when X-rays emitted from the X-ray source 11 can be substantially regarded as parallel beams is expressed by the following expression (8), and the distance $L_2$ is set to a value in a range which satisfies the following expression (9).

[Expression 8]

$$Z = m \frac{p_1^2}{\lambda} \qquad (8)$$

[Expression 9]

$$L_2 < \frac{p_1^2}{\lambda} \qquad (9)$$

In order to generate a periodic pattern image with high contrast, it is preferable that the X-ray blocking sections 31b and 32b block (absorb) X-rays completely. However, even if the above-described materials (gold, platinum, and the like) with excellent X-ray absorption properties are used, there are quite a few X-rays transmitted through the X-ray blocking sections 31b and 32b without being absorbed. For this reason, in order to improve the X-ray blocking ability, it is preferable to set the thicknesses h1 and h2 of the X-ray blocking sections 31b and 32b as large as possible. For example, when the tube voltage of the X-ray tube 18 is 50 kV, it is preferable to block 90% or more of emitted X-rays. In this case, the thicknesses h1 and h2 are 30 μm or more in the case of gold (Au).

On the other hand, if the thicknesses $h_1$ and $h_2$ of the X-ray blocking sections 31b and 32b are set too large, it is difficult for X-rays obliquely incident on the first and second transmission type gratings 31 and 32 to pass through a slit section. As a result, since shade occurs, there is a problem in that an effective field of view in a direction (x direction) perpendicular to the extending direction (strip direction) of the X-ray blocking sections 31b and 32b becomes narrow. Therefore, the upper limits of the thicknesses $h_1$ and $h_2$ are specified in terms of ensuring the field of view. In order to ensure the length V of the effective field of view in the x direction on the detection surface of the FPD 30, assuming that the distance from the X-ray focal point 18b to the detection surface of the FPD 30 is L, the thicknesses $h_1$ and $h_2$ need to be set to satisfy the following expressions (10) and (11) from the geometrical relationship shown in FIG. 5.

[Expression 10]

$$h_1 \le \frac{L}{V/2} d_1 \qquad (10)$$

[Expression 11]

$$h_2 \le \frac{L}{V/2} d_2 \qquad (11)$$

For example, in the case where $d_1$=2.5 μm and $d_2$=3.0 μm and L=2 m in consideration of a normal examination at the hospital, it is preferable that the thickness $h_1$ is set to 100 μm or less and the thickness $h_2$ is set to 120 μm or less in order to ensure the length of 10 cm as the length V of the effective field of view in the x direction.

In the first and second transmission type gratings 31 and 32 configured as described above, an intensity-modulated image is formed by superposition of the G1 image of the first transmission type grating 31 and the second transmission type grating 32 and is then imaged by the FPD 30. There is a slight difference between a pattern period $p_1'$ of the G1 image at the position of the second transmission type grating 32 and a substantial grating pitch $p_2'$ (substantial pitch after manufacturing) of the second transmission type grating 32 due to a manufacturing error or an arrangement error. The arrangement error means that a substantial pitch in the x direction changes due to relative inclination or rotation of the first and second transmission type gratings 31 and 32 or change in the distance therebetween.

By the slight difference between the pattern period $p_1'$ of the G1 image and the grating pitch $p_2'$, the image contrast becomes moiré fringes. A period T of the moiré fringes is expressed by the following expression (12).

[Expression 12]

$$T = \frac{p1' \times p2'}{|p1' - p2'|} \quad (12)$$

In order to detect the moiré fringes with the FPD 30, it is preferable that the array pitch P of the pixels 40 in the x direction should satisfy at least the following expression (13) and further satisfies the following expression (14) (here, n is a positive integer).

[Expression 13]

$$p \ne nT \quad (13)$$

[Expression 14]

$$P < T \quad (14)$$

Expression (13) means that the array pitch P is not an integral multiple of the moiré period T, and moiré fringes can be detected theoretically even in the case of n≧2. Expression (14) means setting the array pitch P to be smaller than the moiré period T.

The array pitch P of the pixels 40 of the FPD 30 is a value (normally about 100 μm) determined by design and is difficult to change. Accordingly, in order to adjust the size relationship between the array pitch P and the moiré period T, it is preferable to change the moiré period T by changing at least one of the pattern period $p_1'$ of the G1 image and the grating pitch $p_2'$ through positional adjustment of the first and second transmission type gratings 31 and 32.

Figure 6A:
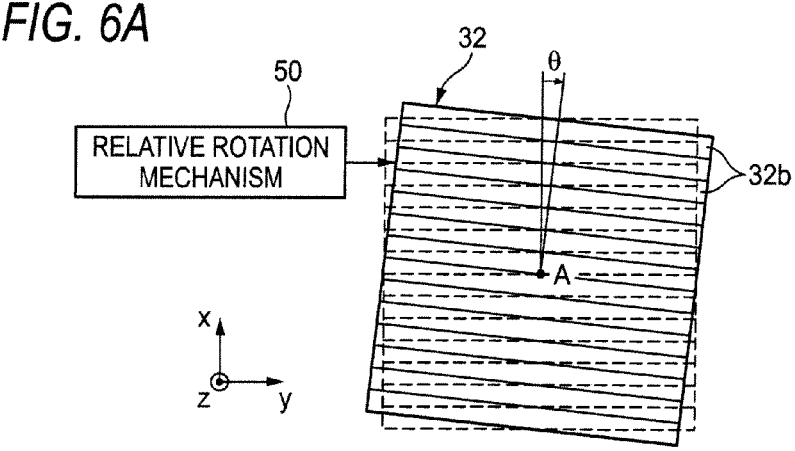
FIGS. 6A to 6C are schematic views showing mechanisms for changing a period of moiré fringes by superposition of first and second transmission type gratings.
Figure 6B:
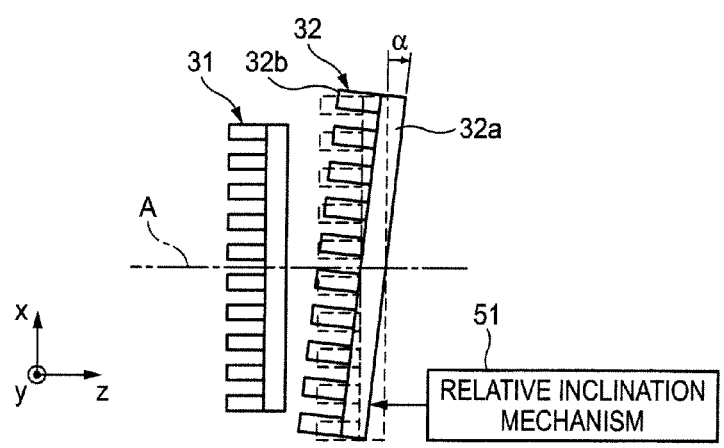
Figure 6C:
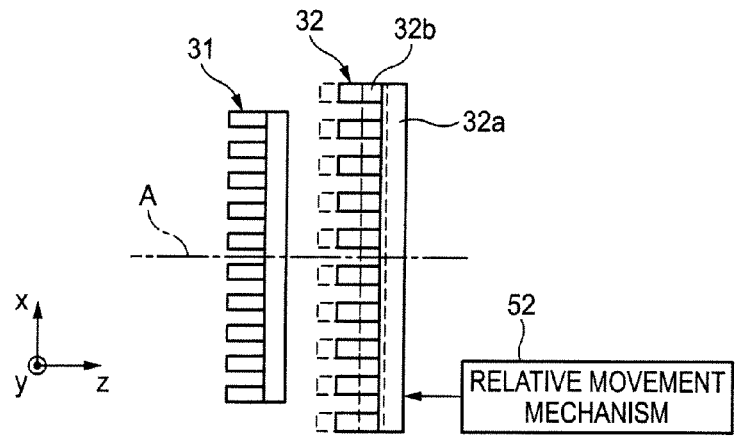

FIGS. 6A to 6C show a method of changing the moiré period T. The change of the moiré period T can be made by rotating one of the first and second transmission type gratings 31 and 32 relative to the other one with the optical axis A as the center. For example, a relative rotation mechanism 50 which rotates the second transmission type grating 32 relative to the first transmission type grating 31 with the optical axis A as the center is provided. If the second transmission type grating 32 is rotated by an angle θ by the relative rotation mechanism 50, the substantial grating pitch in the X-direction changes from $p_2'$ to $p_2'$/cos θ and as a result, the moiré period T changes (FIG. 6A).

As another example, the change of the moiré period T can be made by inclining one of the first and second transmission type gratings 31 and 32 relative to the other one with an axis, which is perpendicular to the optical axis A and positioned along the y direction, as the center. For example, a relative inclination mechanism 51 which inclines the second transmission type grating 32 relative to the first transmission type grating 31 with an axis, which is perpendicular to the optical axis A and positioned along the y direction, as the center is provided. If the second transmission type grating 32 is inclined by an angle α by the relative inclination mechanism 51, the substantial grating pitch in the X-direction changes from $p_2'$ to $p_2'$×cos α and as a result, the moiré period T changes (FIG. 6B).

As still another example, the change of the moiré period T can be made by moving one of the first and second transmission type gratings 31 and 32 relative to the other one along the direction of the optical axis A. For example, a relative movement mechanism 52 which moves the second transmission type grating 32 relative to the first transmission type grating 31 along the direction of the optical axis A so that the distance $L_2$ between the first and second transmission type gratings 31 and 32 is changed is provided. If the second transmission type grating 32 is moved by the amount of movement 6 along the direction of the optical axis A by the relative movement mechanism 52, the pattern period of the G1 image of the first transmission type grating 31 projected on the position of the second transmission type grating 32 changes from $p_1'$ to $p_1' \times (L_1+L_2+\delta)/(L_1+L_2)$ and as a result, the moiré period T changes (FIG. 6C).

In this X-ray imaging system 10, the imaging unit 12 is not a Talbot interferometer as described above and the distance $L_2$ can be freely set. Accordingly, it is possible to appropriately adopt a mechanism which changes the moiré period T by change of the distance $L_2$ like the relative movement mechanism 52. The above-described change mechanisms (the relative rotation mechanism 50, the relative inclination mechanism 51, and the relative movement mechanism 52) of the first and second transmission type gratings 31 and 32 for changing the moiré period T are formed by actuators, such as a piezoelectric element.

When the subject H is disposed between the X-ray source 11 and the first transmission type grating 31, moiré fringes detected by the FPD 30 are modulated by the subject H. The amount of modulation is proportional to an angle of an X-ray deflected by the refraction effect at the subject H. Therefore, a phase contrast image of the subject H can be generated by analyzing the moiré fringes detected by the FPD 30.

Next, a method of analyzing moiré fringes will be described.

Figure 7:
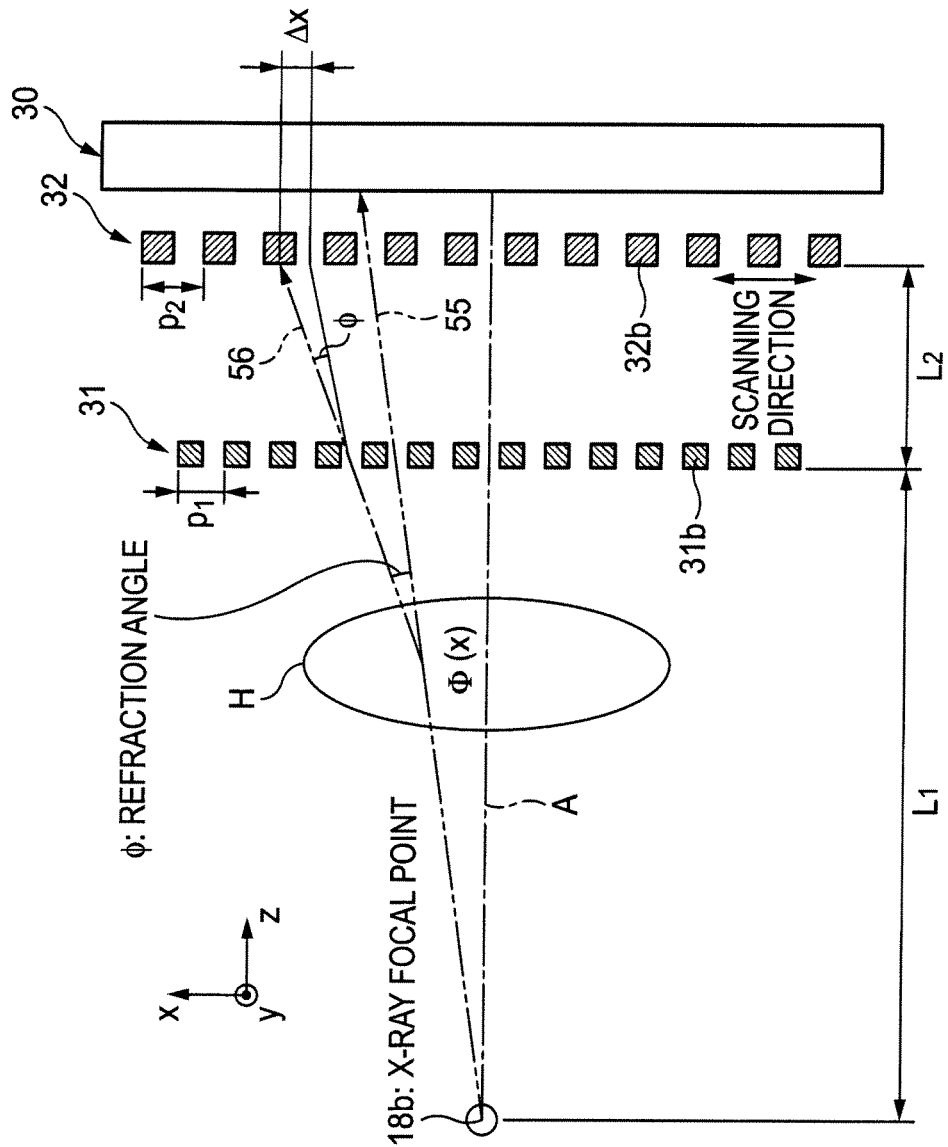
FIG. 7 is a schematic view for explaining the refraction of radiation at a subject.

FIG. 7 shows one X-ray refracted according to the phase shift distribution Φ(x) of the subject H in the x direction. Reference numeral 55 indicates the path of an X-ray going straight when there is no subject H. The X-ray going along the path 55 passes through the first and second transmission type gratings 31 and 32 and is then incident on the FPD 30. Reference numeral 56 indicates the path of an X-ray deflected by refraction at the subject H when the subject H exists. The X-ray going along the path 56 passes through the first transmission type grating 31 and is then blocked by the second transmission type grating 32.

The phase shift distribution Φ(x) of the subject H is expressed by the following expression (15) assuming that the refractive index distribution of the subject H is n(x, z) and z is a direction in which X-rays move.

[Expression 15]

$$\Phi(x) = \frac{2\pi}{\lambda} \int [1 - n(x, z)] dz \quad (15)$$

A G1 image projected from the first transmission type grating 31 onto the position of the second transmission type grating 32 is displaced in the x direction by the amount corresponding to the refraction angle φ due to refraction of X-rays at the subject H. This amount of displacement Δx is approximately expressed by the following expression (16) on the basis of a fact that the refraction angle φ of X-rays is small.

[Expression 16]

$$\Delta x \approx L_2 \phi \quad (16)$$

Here, the refraction angle φ is expressed by the following expression (17) using the X-ray wavelength λ and the phase shift distribution Φ(x) of the subject H.

[Expression 17]

$$\varphi = \frac{\lambda}{2\pi} \frac{\partial \Phi(x)}{\partial x} \quad (17)$$

Thus, the amount of displacement Δx of the G1 image by refraction of X-rays at the subject H is associated with the phase shift distribution Φ(x) of the subject H. In addition, the amount of displacement Δx is related, like the following expression (18), with the amount of phase shift ψ of an intensity-modulated signal (amount of phase shift of an intensity-modulated signal of each pixel 40 in each of the cases when there is the subject H and when there is no subject H) output from each pixel 40 of the FPD 30.

[Expression 18]

$$\Psi = \frac{2\pi}{p_2} \Delta x = \frac{2\pi}{p_2} L_2 \varphi \quad (18)$$

Accordingly, by calculating the amount of phase shift ψ of the intensity-modulated signal of each pixel 40, the refraction angle φ is calculated from expression (18). In addition, the differential amount of the phase shift distribution Φ(x) is calculated using expression (17). By integrating this for x, the phase shift distribution Φ(x) of the subject H may be generated. A phase contrast images of the subject H can be generated with use of the amount of phase shift ψ, the refraction angle φ and the shapes shift distribution Φ(x). In the X-ray imaging system 10, the amount of phase shift ψ is calculated using a fringe scanning method shown below.

In the fringe scanning method, imaging is performed while performing translational movement of one of the first and second transmission type gratings 31 and 32 relative to the other one in a stepwise manner in the x direction (that is, imaging is performed while changing the phases of lattice periods of both the first and second transmission type gratings 31 and 32). Although the second transmission type grating 32 is moved by the scanning mechanism 33 in the X-ray imaging system 10, the first transmission type grating 31 may be moved. When moire fringes move according to the movement of the second transmission type grating 32 and the distance of translational movement (amount of movement in the x direction) amounts to one period (grating pitch $p_2$) of the lattice period of the second transmission type grating 32 (that is, when a phase change amounts to 2π), the moiré fringes return to the original positions. By capturing fringe images according to such a change of moiré fringes by the FPD 30 while moving the second transmission type grating 32 gradually by the amount obtained by dividing the grating pitch $p_2$ by an integer, acquiring an intensity-modulated signal of each pixel 40 from the plurality of captured fringe images, and performing arithmetic processing by the arithmetic processing section 22, the amount of phase shift ψ of the intensity-modulated signal of each pixel 40 is acquired.

Figure 8:
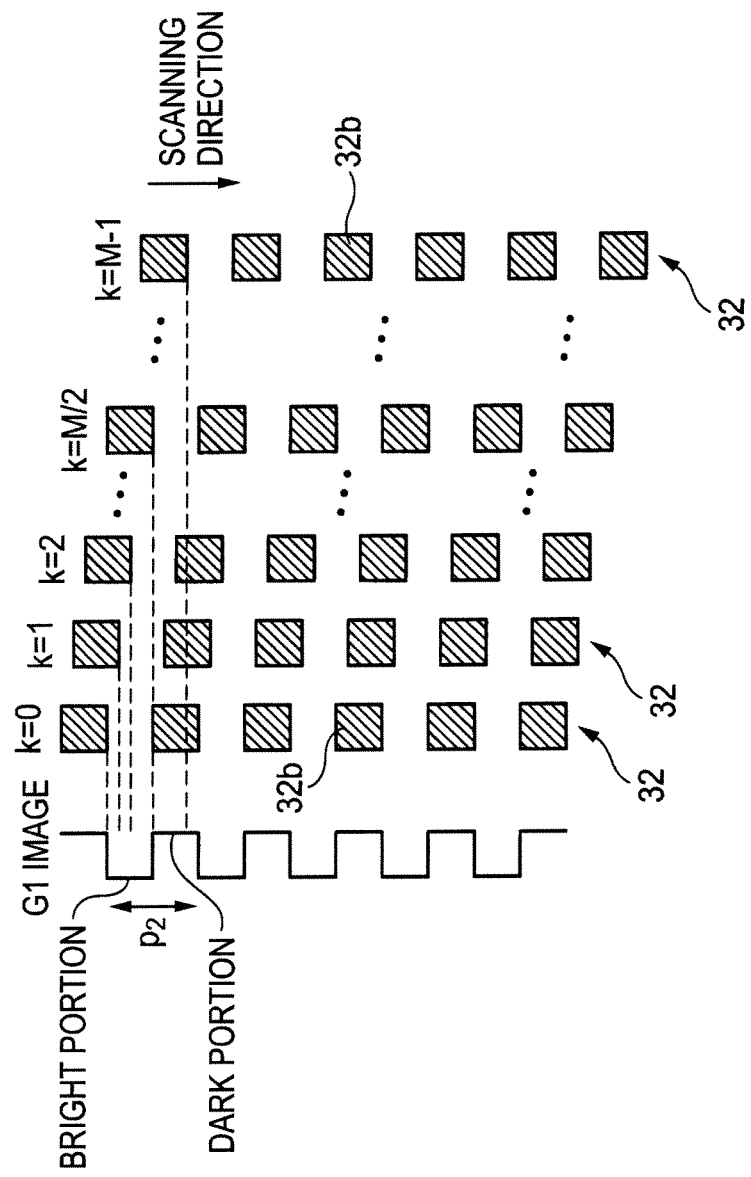
FIG. 8 is a schematic view for explaining a fringe scanning method.

FIG. 8 is a schematic view showing a state where the second transmission type grating 32 is gradually moved by a scanning pitch ($p_2/M$) obtained by dividing the grating pitch $p_2$ by M (integers of 2 or more). The scanning mechanism 33 performs translational movement of the second transmission type grating 32 sequentially at M scanning positions (k=0, 1, 2, ..., M−1). In FIG. 8, the initial position of the second transmission type grating 32 is set as a position (k=0) at which a dark portion of a G1 image at the position of the second transmission type grating 32 when there is no subject H almost matches the X-ray blocking sections 32b. However, the initial position may be any of the M scanning positions (k=0, 1, 2, ..., M−1).

First, at the position of k=0, X-rays which are not refracted by the subject H are mainly transmitted through the second transmission type grating 32. Then, as the second transmission type grating 32 moves in order of k=1, 2, ..., X-ray components which were not refracted by the subject H among X-rays transmitted through the second transmission type grating 32 is decreased while X-ray components refracted by the subject H is increased. Especially at the position of k=M/2, only the X-rays refracted by the subject H are mainly transmitted through the second transmission type grating 32. If the position exceeds k=M/2, X-ray components refracted by the subject H among X-rays transmitted through the second transmission type grating 32 are decreased while X-ray components which are not refracted by the subject H are increased conversely.

By imaging at each position of k=0, 1, 2, ..., M−1 using the FPD 30, M pixel data items are obtained for each pixel 40. Hereinafter, a method of calculating the amount of phase shift ψ of an intensity-modulated signal of each pixel 40 from the M pixel data items will be described. If the pixel data (signal value) of each pixel 40 at the position k of the second transmission type grating 32 is denoted as $I_k(x)$, $I_k(x)$ is expressed by the following expression (19).

[Expression 19]

$$I_k(x) = A_0 + \sum_{n>0} A_n \exp\left[2\pi i \frac{n}{p_2} \left\{ L_2 \varphi(x) + \frac{kp_2}{M} \right\} \right] \quad (19)$$

Here, x is a coordinate of a pixel in the x direction, $A_0$ is an intensity of an incident X-ray, and $A_n$ is a value corresponding to the contrast of an intensity-modulated signal (here, n is a positive integer). In addition, φ(x) expresses the above-described refraction angle φ as a function of the coordinate x of the pixel 40.

Then, using the relational expression of the following expression (20), the above-described refraction angle φ(x) is expressed by the following expression (21).

[Expression 20]

$$\sum_{k=0}^{M-1} \exp\left(-2\pi i \frac{k}{M}\right) = 0 \quad (20)$$

[Expression 21]

$$\varphi(x) = \frac{p_2}{2\pi L_2} \arg\left[\sum_{k=0}^{M-1} I_k(x) \exp\left(-2\pi i \frac{k}{M}\right)\right] \quad (21)$$

Here, arg[ ] means calculation of an angle of deviation and corresponds to the amount of phase shift ψ of an intensity-modulated signal of each pixel 40. Accordingly, the refraction angle φ(x) can be acquired by calculating the amount of phase shift ψ of an intensity-modulated signal of each pixel 40, on the basis of expression (21), from the M pixel data items obtained in each pixel 40.

Figure 9:
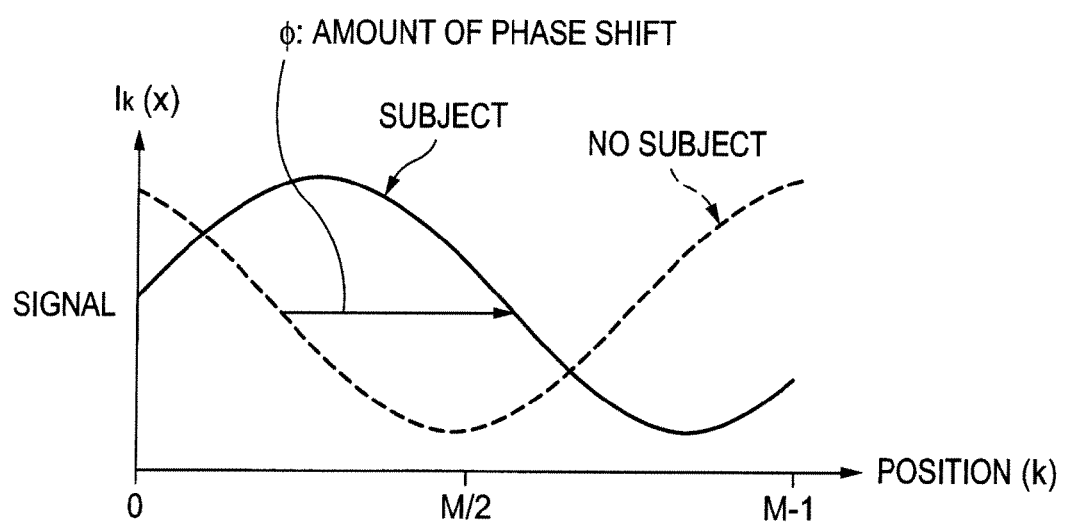
FIG. 9 is a graph showing a signal of a pixel of a radiation image detector according to fringe scanning.

Specifically, M pixel data items obtained in each pixel 40 periodically change with the position k of the second transmission type grating 32 at periods of the grating pitch $p_2$, as shown in FIG. 9. In FIG. 9, a dotted line indicates a change of pixel data when there is no subject H, and a solid line indicates a change of pixel data when there is the subject H. A phase difference between these two waveforms corresponds to the amount of phase shift ψ of an intensity-modulated signal of each pixel 40.

In addition, the refraction angle φ(x) is a value corresponding to the differential phase value as shown in expression (17) given above. Accordingly, the phase shift distribution Φ(x) is obtained by integrating the refraction angle φ(x) along the x axis.

In the above explanation, the y coordinate of the pixel 40 in the y direction is not taken into consideration. However, the two-dimensional phase shift distribution Φ(x, y) in the x and y directions is acquired by performing the same operation for each y coordinate.

Next, a method of correcting the phase shift distribution Φ(x) in the X-ray imaging system 10 will be described.

Figure 10:
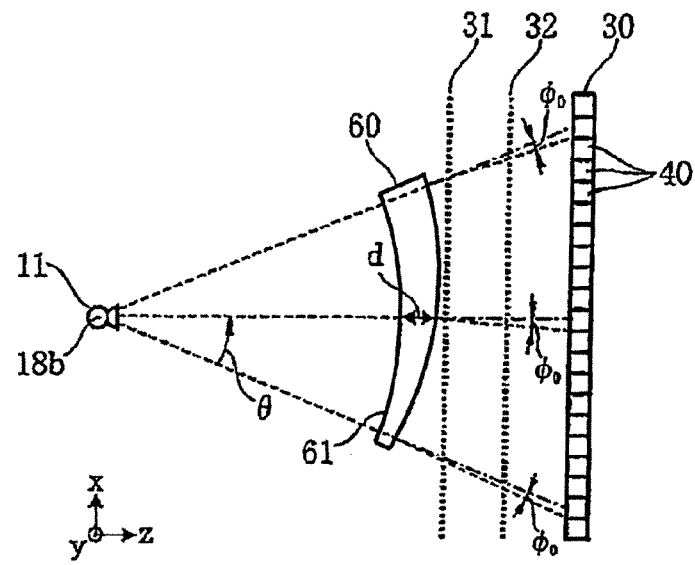
FIG. 10 is a schematic view showing an example of a phantom used for sensitivity correction of the radiographic system shown in FIG. 1.

FIG. 10 shows an example of a phantom used for sensitivity correction of the X-ray imaging system 10.

A phantom 60 has an incidence surface 61, which is an arc having the X-ray focal point 18b of the X-ray source 11 as the center, on the cross section along the x direction. Although X-rays emitted from the X-ray source 11 are cone beams and spread radially in the x direction with the X-ray focal point 18b as the center, the X-rays emitted from the X-ray source 11 are incident perpendicular to each portion of the incidence surface 61 because the incidence surface 61 is an arc having the X-ray focal point 18b as the center.

In addition, the thickness d of the phantom 60 changes linearly with the central angle θ around the X-ray focal point 18b, and the central angle θ and the thickness d satisfy the following expression (22).

[Expression 22]

$$\frac{\partial d}{\partial \theta} = k \quad (22)$$

Here, "k" is a constant. X-rays incident on the phantom 60 configured as described above are transmitted through the phantom 60 with the same refraction angle $\phi_0$ in the x direction and are then incident on each pixel 40 of the FPD 30.

In the sensitivity correction of the X-ray imaging system 10 using the phantom 60, the image data of each pixel 40 of the FPD 30 in each step is acquired by performing imaging of the phantom 60 while performing translational movement of one of the first and second transmission type gratings 31 and 32 relative to the other one in a stepwise manner in the x direction. Then, from the plurality of acquired pixel data of each pixel 40, the refraction angle φ(x) of each pixel 40 is calculated on the basis of expression (21).

$\phi_0/\phi(x)$, which is a ratio of the refraction angle $\phi_0$ given to X-rays by the phantom 60 to the refraction angle φ(x) obtained by calculation, is set as a correction coefficient of each pixel 40 and stored in the storage section 23 as a sensitivity correction map. Then, a distribution image of the refraction angle φ(x) (and the phase differential value) is acquired by imaging a subject, and it is corrected by multiplying the pixel value of each pixel, which forms the distribution image, by the correction coefficient $\phi_0/\phi(x)$ of the pixel 40 of the FPD 30 corresponding to the pixel referring to the sensitivity correction map stored in the storage section 23. A phase contrast image is generated on the basis of the distribution of the refraction angle φ(x) obtained by correction. Thus, it is possible to perform correction which reflects error factors included in the imaging system, such as an error of the grating pitch $p_2$ of the second transmission type grating 32, a change in the distance $L_2$ between the first and second transmission type gratings 31 and 32, and a difference between the effective widths of the pixels 40 of the FPD 30.

When calculating the correction coefficient of each pixel 40, it is preferable to use the phantom 60 which gives the same refraction angle $\phi_0$ to X-rays transmitted through pixels. In this case, the correction coefficient of each pixel 40 can be easily acquired by calculating the ratio of the same refraction angle $\phi_0$ to the refraction angle φ(x) obtained by calculation. Here, any phantom may be used as long as the refraction angle given to X-rays by the phantom is known. In this case, it is preferable that the correction coefficient of each pixel 40 is set as φ'(x)/φ(x) assuming that the refraction angle of an X-ray incident on each pixel 40, which is given by the phantom, is φ'(x).

The above calculation is performed by the arithmetic processing section 22, and the arithmetic processing section 22 stores the generated phase shift distribution Φ(x, y) in the storage section 23 as a phase contrast image. In addition, the phase shift distribution Φ is the integral of a differential amount of the phase shift distribution Φ calculated from the refraction angle φ, and the differential amounts of the refraction angle φ and the phase shift distribution Φ are also associated with a phase change of X-rays by the subject. Accordingly, the differential amount of the refraction angle φ or the phase shift distribution Φ may also be regarded as a phase contrast image.

The fringe scanning and the processing of generating a phase contrast image described above are automatically performed by cooperation of respective sections based on the control of the control device 20 after an operator gives an imaging instruction through the input device 21 and a phase contrast image of the subject H is finally displayed on the monitor 24.

According to the X-ray imaging system 10 described above, it is possible to correct a plurality of imaging errors caused by a plurality of error factors included in the imaging system, such as an error of the grating pitch $p_2$ of the second transmission type grating 32, a change in the distance $L_2$ between the first and second transmission type gratings 31 and 32, and a difference between the effective widths of the pixels 40 of the FPD 30. In addition, since a plurality of errors caused by a plurality of error factors can be corrected simultaneously instead of correcting an error caused by each error factor separately, the correction can be performed easily and precisely. Accordingly, the precision of phase imaging can be improved.

In addition, according to the X-ray imaging system 10 described above, most X-rays are not diffracted at the first transmission type grating 31 but projected onto the second transmission type grating 32 geometrically. Accordingly, since high spatial coherence is not required for emitted X-rays, a normal X-ray source used in the medical field can be used as the X-ray source 11. In addition, the distance $L_2$ from the first transmission type grating 31 to the second transmission type grating 32 can be set to any value. Accordingly, since the distance $L_2$ can be set to be smaller than the minimum Talbot interference distance in the Talbot interferometer, the imaging unit 12 can be made small (thin). In addition, according to the X-ray imaging system 10, almost all wavelength components of emitted X-rays contribute to a projected image (G1 image) from the first transmission type grating 31. Accordingly, since the contrast of moiré fringes is improved, the detection sensitivity of a phase contrast image can be improved.

Moreover, in the X-ray imaging system 10 described above, the refraction angle φ is calculated by performing fringe scanning on a projected image of the first transmission type grating 31. For this reason, both the first and second transmission type gratings 31 and 32 are absorption type gratings in the above explanation. However, the invention is not limited to this. Also in the case where the refraction angle φ is calculated by performing fringe scanning on a Talbot interference image as described above, the invention is useful because the refraction angle φ depends on the grating pitch $p_2$ of the second transmission type grating 32, the distance $L_2$ between the first and second transmission type gratings 31 and 32, and the effective width of each pixel 40 of the FPD 30. Therefore, the first transmission type grating 31 may be not only an absorption type grating but also a phase type grating.

Moreover, although moiré fringes formed by superposition of a projected image of the first transmission type grating 31 and the second transmission type grating 32 are analyzed by the fringe scanning method in the X-ray imaging system 10 described above, the method of analyzing moiré fringes is not limited to the fringe scanning method. For example, it is also possible to adopt various methods using moiré fringes, such as a method using the Fourier transform/inverse Fourier transform known from "J. Opt. Soc. Am. Vol. 72, No. 1 (1982) p. 156".

Hereinafter, a method of analyzing moiré fringes using the Fourier transform/inverse Fourier transform will be described. Moiré fringes formed by the first and second transmission type gratings 31 and 32, in which the X-ray blocking sections 31b and 32b extend in the y direction, are expressed by the following expression (23). Accordingly, expression (23) can be rewritten as the following expression (24).

[Expression 23]

$$I(x,y)=a(x,y)+b(x,y)\cos(2\pi f_0 x+\phi(x,y)) \qquad (23)$$

[Expression 24]

$$I(x,y)=a(x,y)+c(x,y)\exp(2\pi i f_0 x)+c^*(x,y)\exp(-2\pi i f_0 x) \qquad (24)$$

In expression (23), a(x, y) indicates a background, b(x, y) indicates an amplitude of a basic frequency component of a moiré, and $f_0$ indicates a basic frequency of a moiré. Moreover, in expression (24), c(x, y) is expressed by the following expression (25).

[Expression 25]

$$c(x,y) = \frac{1}{2}b(x,y)\exp[i\varphi(x,y)] \qquad (25)$$

Accordingly, the information regarding the refraction angle φ(x, y) can be acquired by extracting components of c(x, y) or c*(x, y) from the moiré fringes. Here, expression (25) becomes the following expression (26) by the Fourier transform.

[Expression 26]

$$I(f_x,f_y)=A(f_x,f_y)+C(f_x-f_0,f_y)+C^*(f_x+f_0,f_y) \qquad (26)$$

In expression (26), $I(f_x, f_y)$, $A(f_x, f_y)$, and $C(f_x, f_y)$ are two-dimensional Fourier transforms with respect to I(x, y), a(x, y), and c(x, y), respectively.

In a spectrum pattern of moiré fringes, three peaks usually occur. Specifically, the peaks resulting from $C(f_x, f_y)$ and $C^*(f_x, f_y)$ occur at both sides with the peak resulting from $A(f_x, f_y)$ interposed therebetween. A region including the peak resulting from $C(f_x, f_y)$ or $C^*(f_x, f_y)$ is cut and the peak resulting from the cut $C(f_x, f_y)$ or $C^*(f_x, f_y)$ is moved to the origin of the frequency space and inverse Fourier transform is performed. As a result, the refraction angle φ(x, y) can be acquired from the obtained complex number information.

In addition, although the subject H is disposed between the X-ray source 11 and the first transmission type grating 31 in the X-ray imaging system 10 described above, the phase contrast image can also be generated similarly when the subject H is disposed between the first and second transmission type gratings 31 and 32.

Figure 11:
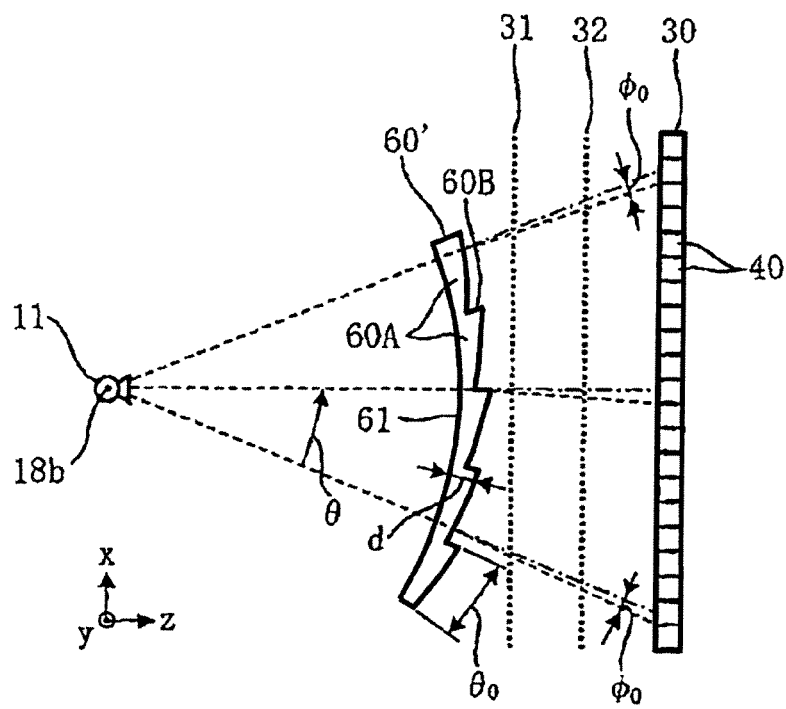
FIG. 11 is a schematic view showing a modification of the phantom shown in FIG. 10.

FIG. 11 shows a modification of the phantom shown in FIG. 10. A phantom 60' shown in FIG. 11 has an incidence surface 61, which is an arc having the X-ray focal point 18b of the X-ray source 11 as the center, on the cross section along the x direction. Moreover, a change in the thickness d of the phantom 60' is periodically repeated. The thickness d in a range of one period changes linearly in the central angle θ around the X-ray focal point 18b.

X-rays incident on each linear section 60A, the thickness d of which changes linearly, of the phantom 60' configured as described above are transmitted through the phantom 60' with the same refraction angle $\phi_0$ in the x direction and are then incident on each pixel 40 of the FPD 30. Since the phantom 60' is configured such that a change in the thickness d is periodically repeated, the thickness can be made smaller than that in the phantom 60 shown in FIG. 10. In addition, the phantom 60' may be entirely formed by one member or may be formed by separately forming the plurality of linear sections 60A, each of which corresponds to one period of a periodic change of the thickness d, and connecting them to each other.

Here, although the same refraction angle $\phi_0$ is given to X-rays incident on the linear section 60A, X-rays incident on a step-like connecting section 60B, which is a small region between the adjacent linear sections 60A, may be transmitted through the phantom 60' with a different refraction angle from the refraction angle $\phi_0$ given in the linear section 60A due to discontinuity in the thickness d in the connecting section 60B. If a correction coefficient in the pixel 40 on which X-rays with a different refraction angle from $\phi_0$ are incident is set to $\phi_0/\phi(x)$ like the other pixels 40, an error is included in the correction coefficient. Therefore, preferably, the correction coefficient of each pixel 40 is calculated by imaging the phantom 60' a plural number of times while rotating the phantom 60' gradually by a predetermined angle around the X-ray focal point 18b.

For example, the case is assumed in which the phantom 60' is imaged twice. First, first imaging is performed and the refraction angle φ1(x) of each pixel 40 is calculated, on the basis of expression (20), from a plurality of pixel data items acquired in each pixel 40.

Figure 12:
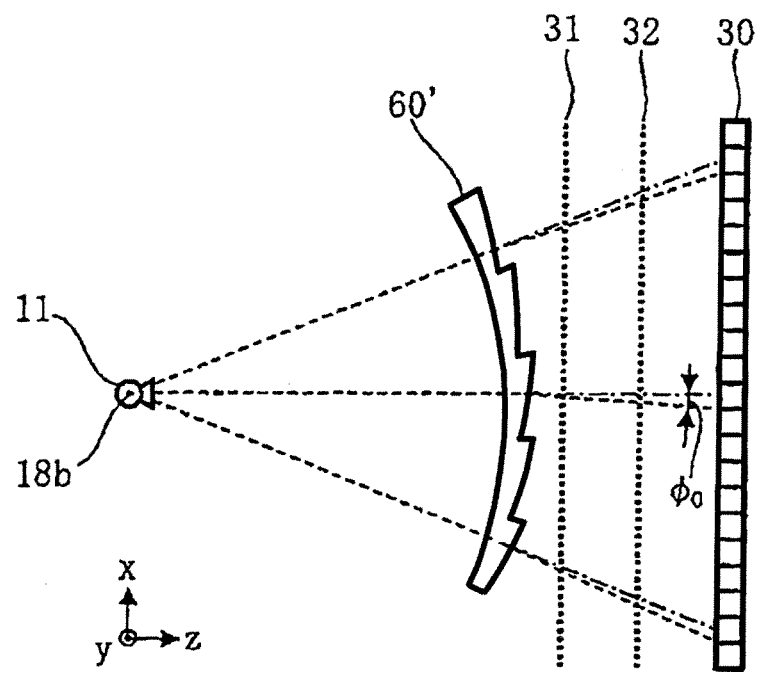
FIG. 12 is a schematic view showing a correction method using the phantom shown in FIG. 11.

Then, as shown in FIG. 12, second imaging is performed after rotating the phantom 60' around the X-ray focal point 18b by a predetermined angle (for example, θ$_0$×1/2) excluding the integral multiples of the central angle θ$_0$ around the X-ray focal point 18b, which corresponds to one period (one linear section 60A) in a periodic change of the thickness d and the refraction angle φ2(x) of each pixel 40 is calculated, on the basis of expression (21), from a plurality of pixel data items acquired in each pixel 40.

For the pixel 40 on which X-rays transmitted through the connecting section 60B by the first imaging are incident, the refraction angle φ1(x) of the pixel 40 calculated by the first imaging is disregarded and the refraction angle φ2(x) of the pixel 40 calculated by the second imaging is used, and φ$_0$/φ2(x) is set as a correction coefficient of the pixel 40. For the other pixels 40, the refraction angle φ1(x) calculated by the first imaging is used, and φ$_0$/φ1(x) is set as a correction coefficient of the pixel 40. Accordingly, since an influence of non-uniform refraction angles given to X-rays at the linear section 60A and the connecting section 60B can be removed, it is possible to calculate a correction coefficient of each pixel 40 precisely.

Alternatively, it is also possible to calculate the average of a plurality of refraction angles φ1(x), φ2(x), . . . of each pixel 40 calculated by each imaging and to set φ$_0$/φ$_{avg}$(x) as a correction coefficient of the pixel 40 using the average refraction angle φ$_{avg}$(x). Also in this case, since it is possible to reduce an influence of non-uniform refraction angles given to X-rays at the linear section 60A and the connecting section 60B, the correction coefficient of each pixel 40 can be precisely calculated.

Figure 13:
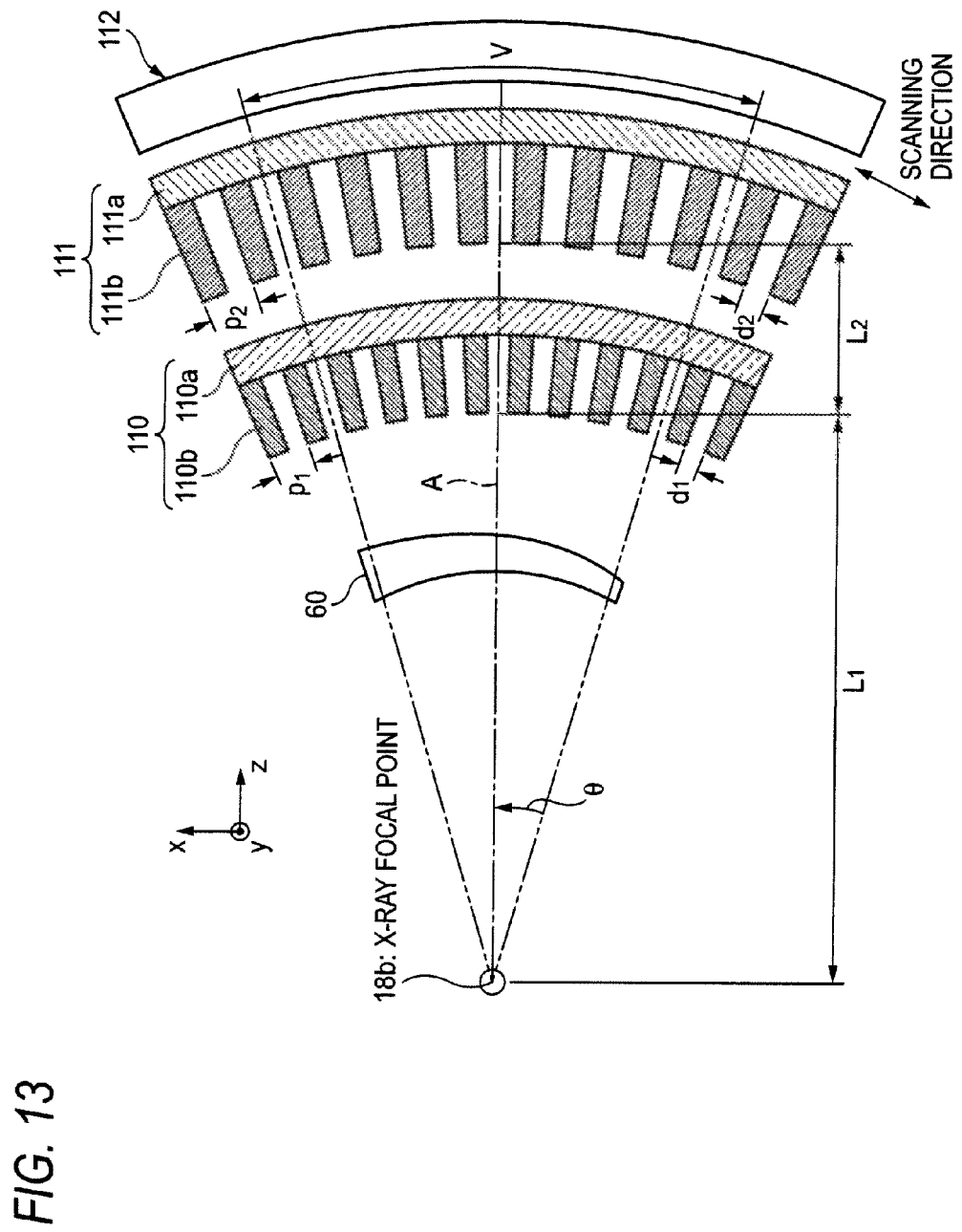
FIG. 13 is a schematic view showing a modification of the radiographic system shown in FIG. 1.

The first and second transmission type gratings 31 and 32 of the X-ray imaging system 10 described above are configured to have linear shapes (that is, flat lattice surfaces) in the periodic arrangement direction of the X-ray blocking sections 31b and 32b. However, as shown in FIG. 13, first and second transmission type gratings 110 and 111 with curved lattice surfaces as recessed surfaces may also be used instead.

In the first transmission type grating 110, a plurality of X-ray blocking sections 110b is periodically arrayed at predetermined pitches p$_1$ on the surface of a substrate 110a which allows X-rays to be transmitted therethrough and which is curved. Each X-ray blocking section 110b extends linearly in the y direction, and the lattice surface of the first transmission type grating 110 has a shape along the cylindrical surface with a straight line, which extends in the extending direction of the X-ray blocking section 110b from the X-ray focal point 18b, as a central axis. Similarly, in the second transmission type grating 111, a plurality of X-ray blocking sections 111b is periodically arrayed at predetermined pitches p$_2$ on the surface of a substrate 111a which allows X-rays to be transmitted therethrough and which is curved. Each X-ray blocking section 111b extends linearly in the y direction, and the lattice surface of the second transmission type grating 111 has a shape along the cylindrical surface with a straight line, which extends in the extending direction of the X-ray blocking section 111b from the X-ray focal point 18b, as a central axis.

Assuming that the distance from the X-ray focal point 18b to the first transmission type grating 110 is L$_1$ and the distance from the first transmission type grating 110 to the second transmission type grating 111 is L$_2$, the grating pitch p$_1$ of the first transmission type grating 110 and the grating pitch p$_2$ of the second transmission type grating 111 are determined so as to satisfy the relationship of expression (5) given above.

By forming the lattice surfaces of the first and second transmission type gratings 110 and 111 in the cylindrical surface shape, all X-rays emitted from the X-ray focal point 18b are incident perpendicular to the lattice surfaces when there is no subject H. As a result, since limitations on the thickness h$_1$ of the X-ray blocking section 110b and the thickness h$_2$ of the X-ray blocking section 111b are reduced, it is not necessary to take expressions (10) and (11) given above into consideration.

In the X-ray imaging system 10 using the first and second transmission type gratings 110 and 111 described above, the refraction angle φ(x) is calculated by performing the above-described fringe scanning by moving one of the first and second transmission type gratings 110 and 111 in a direction along the lattice surface (cylindrical surface) with the X-ray focal point 18b as the center and the phase shift distribution Φ(x) is acquired on the basis of the refraction angle φ(x). In correction of the phase shift distribution Φ(x) using the phantoms 60 and 60', the refraction angle φ(x) depends on the distance L$_2$ between the first and second transmission type gratings 110 and 111, but the distance L$_2$ is constant without changing with the central angle θ around the X-ray focal point 18b. Therefore, it is possible to reduce error factors in phase imaging.

Figure 14:
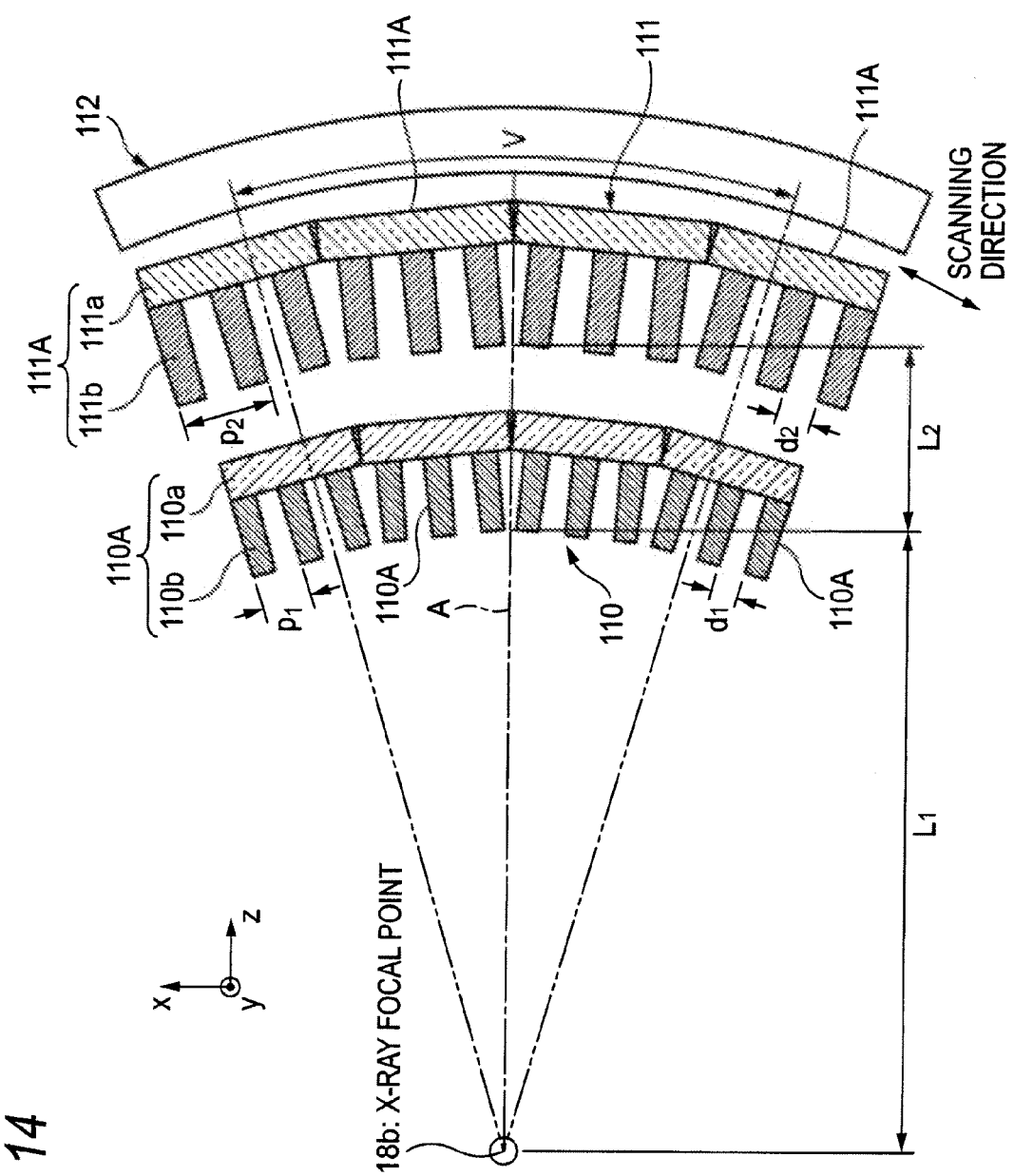
FIG. 14 is a schematic view showing a modification of the radiographic system shown in FIG. 1.

As shown in FIG. 14, it is also possible to form the first transmission type grating 110 by connecting a plurality of grating pieces 110A to each other and to form the second transmission type grating 111 by connecting a plurality of grating pieces 111A to each other.

Since high precision is required for the grating pitches of the first and second transmission type gratings, it is difficult to manufacture the large-sized first and second transmission type gratings. However, by adopting a configuration in which the first and second transmission type gratings are formed by connecting a plurality of grating pieces to each other, each grating piece can be made to be relatively small. As a result, increasing the sizes of the first and second transmission type gratings 110 and 111 and maintaining the precision of a grating pitch can be realized simultaneously.

Moreover, in the case of forming the lattice surfaces of the first and second transmission type gratings 110 and 111 in the cylindrical surface shape, the lattice surfaces can be easily formed in the cylindrical surface shape by connecting two adjacent grating pieces to each other in a state inclined by a predetermined angle.

Figure 15:
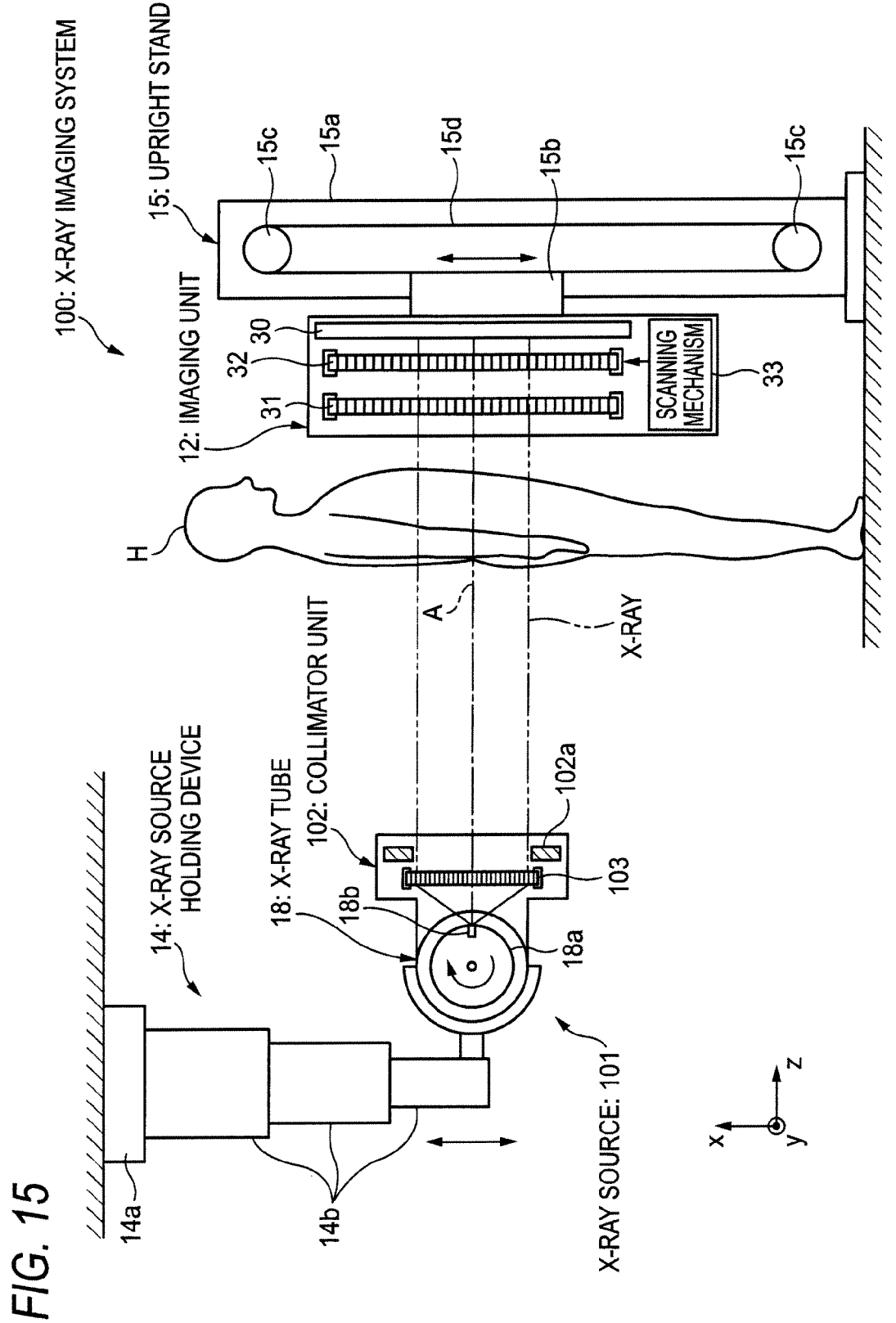
FIG. 15 is a schematic view showing the configuration of an example of a radiographic system for explaining an embodiment of the invention.

FIG. 15 shows another example of an X-ray imaging system. An X-ray imaging system 100 shown in FIG. 15 is different from the above-described X-ray imaging system 10 in that a multi-capillary X-ray lens 103 is provided in a collimator unit 102 of an X-ray source 101. The multi-capillary X-ray lens 103 condenses X-rays emitted from the X-ray focal point 18b and emits X-rays which are almost parallel to each other in the x direction. Since the other configuration is the same as that of the X-ray imaging system 10, the explanation will be omitted.

In this X-ray imaging system 100, similar to the X-ray imaging system 10 described above, the refraction angle φ(x) is calculated by performing the above-described fringe scanning by moving one of the first and second transmission type gratings 31 and 32 relative to the other one in the x direction and the phase shift distribution Φ(x) is acquired on the basis of the refraction angle φ(x).

Next, a method of correcting the phase shift distribution Φ(x) in the X-ray imaging system 100 will be described.

Figure 16:
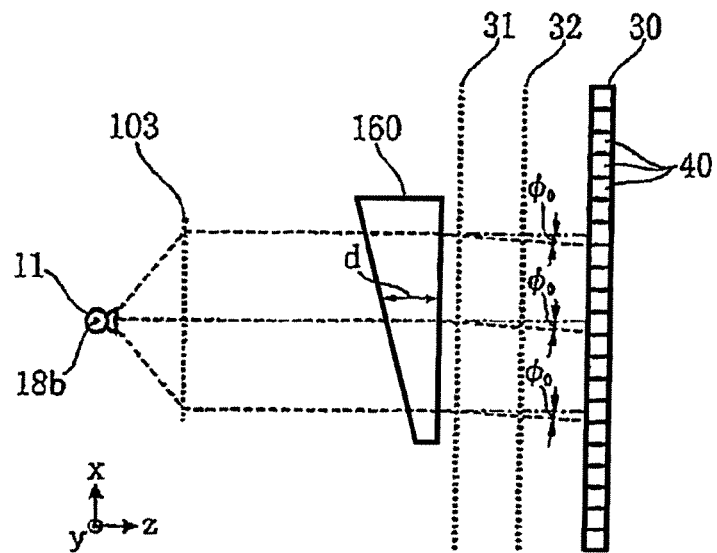
FIG. 16 is a schematic view showing an example of a phantom used for sensitivity correction of the radiographic system shown in FIG. 15.

FIG. 16 shows an example of a phantom used for sensitivity correction of the X-ray imaging system 100.

A phantom 160 has a thickness d which changes linearly in the x direction. X-rays emitted from the X-ray source 101 are incident on the phantom 160 so as to be almost parallel to each other in the x direction. The thickness d of the phantom 160 changes linearly in the x direction, and X-rays which are incident on the phantom 160 so as to be almost parallel to each other in the x direction are transmitted through the phantom 160 with the same refraction angle $\phi_0$ in the x direction and are then incident on each pixel 40 of the FPD 30.

The image data of each pixel 40 of the FPD 30 in each step is acquired by performing imaging of the phantom 60 while performing translational movement of one of the first and second transmission type gratings 31 and 32 relative to the other one in a stepwise manner in the x direction. Then, from the plurality of acquired pixel data of each pixel 40, the refraction angle φ(x) of each pixel 40 is calculated on the basis of expression (21). Then, $\phi_0/\phi(x)$ is set as a correction coefficient of each pixel 40 and stored in the storage section 23 as a sensitivity correction map. Then, a distribution image of the refraction angle φ(x) (and the phase differential value) is acquired by imaging a subject, and it is corrected by multiplying the pixel value of each pixel, which forms the distribution image, by the correction coefficient $\phi_0/\phi(x)$ of the pixel 40 of the FPD 30 corresponding to the pixel referring to the sensitivity correction map stored in the storage section 23. A phase contrast image is generated on the basis of the distribution of the refraction angle φ(x) obtained by correction.

Figure 17:
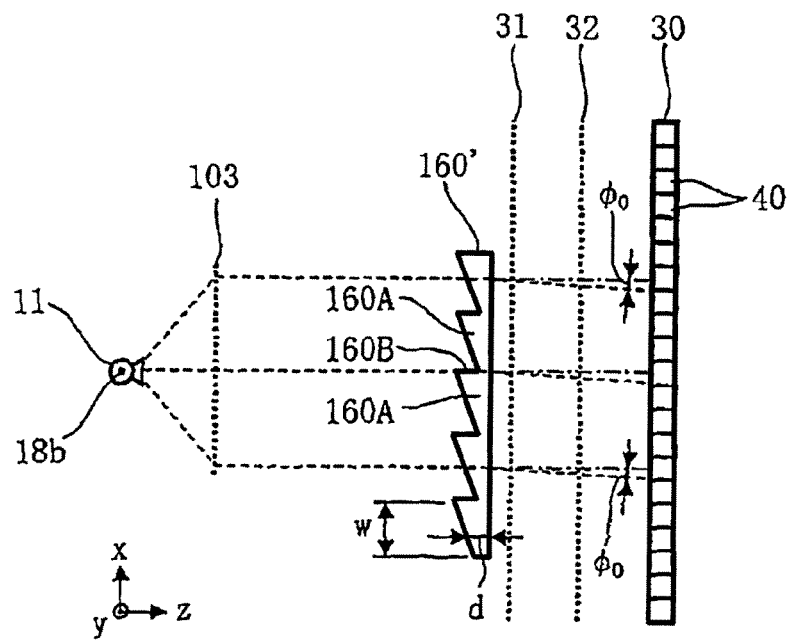
FIG. 17 is a schematic view showing a modification of the phantom shown in FIG. 16.

FIG. 17 shows a modification of the phantom shown in FIG. 16. In a phantom 160' shown in FIG. 17, a change in the thickness d is periodically repeated in the x direction. The thickness d in a range of one period changes linearly in the x direction.

X-rays incident on each linear section 160A, the thickness d of which changes linearly, of the phantom 160' configured as described above are transmitted through the phantom 160' with the same refraction angle $\phi_0$ in the x direction and are then incident on each pixel 40 of the FPD 30. Since the phantom 160' is configured such that a change in the thickness d is periodically repeated, the thickness can be made smaller than that in the phantom 160 shown in FIG. 16. In addition, the phantom 160' may be entirely formed by one member or may be formed by forming the linear section 160A corresponding to one period of a periodic change of the thickness d with one member and connecting the plurality of linear sections 160A to each other.

Here, although the same refraction angle $\phi_0$ is given in the x direction to X-rays incident on the linear section 160A, X-rays incident on a step-like connecting section 160B, which is a small region between the adjacent linear sections 160A, may be transmitted through the phantom 160' with a different refraction angle from the refraction angle $\phi_0$ given in the linear section 160A due to discontinuity in the thickness d in the connecting section 160B. If a correction coefficient in the pixel 40 on which X-rays with a different refraction angle from $\phi_0$ are incident is set to $\phi_0/\phi(x)$ like the other pixels 40, an error is included in the correction coefficient. Therefore, preferably, the correction coefficient of each pixel 40 is calculated by imaging the phantom 160' a plural number of times while moving the phantom 160' in the x direction gradually by a predetermined distance.

For example, the case is assumed in which the phantom 160' is imaged twice. First, first imaging is performed and the refraction angle φ1(x) of each pixel 40 is calculated, on the basis of expression (21), from a plurality of pixel data items acquired in each pixel 40.

Figure 18:
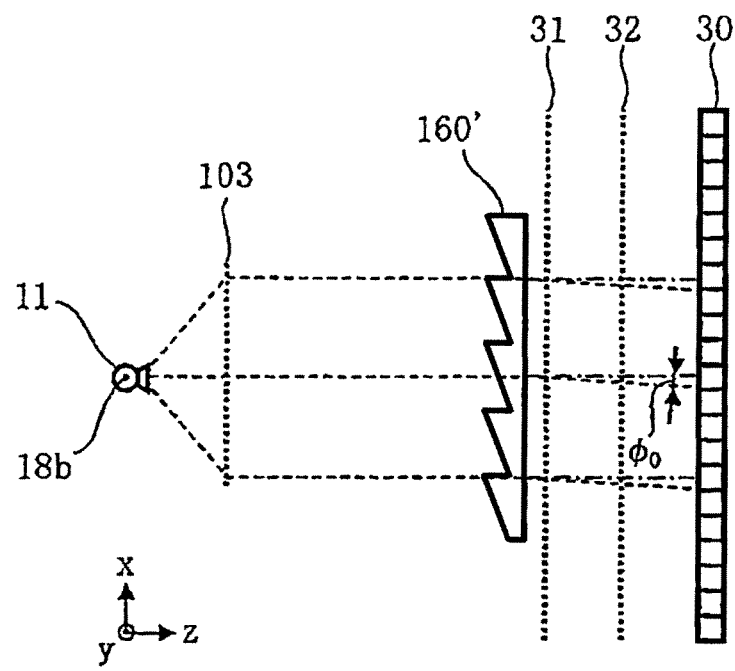
FIG. 18 is a schematic view showing a correction method using the phantom shown in FIG. 17.

Then, as shown in FIG. 18, second imaging is performed after moving the phantom 160' in the x direction by a predetermined distance (for example, w×1/2) excluding the integral multiples of the size w of one period (one linear section 160A) in a periodic change of the thickness d and the refraction angle φ2(x) of each pixel 40 is calculated, on the basis of expression (21), from a plurality of pixel data items acquired in each pixel 40.

For the pixel 40 on which X-rays transmitted through the connecting section 160B by the first imaging are incident, the refraction angle φ1(x) of the pixel 40 calculated by the first imaging is disregarded and the refraction angle φ2(x) of the pixel 40 calculated by the second imaging is used, and $\phi_0/\phi2(x)$ is set as a correction coefficient of the pixel 40. For the other pixels 40, the refraction angle φ1(x) calculated by the first imaging is used, and $\phi_0/\phi1(x)$ is set as a correction coefficient of the pixel 40. Accordingly, since an influence of non-uniform refraction angles given to X-rays at the linear section 160A and the connecting section 160B can be removed, it is possible to calculate a correction coefficient of each pixel 40 precisely.

Alternatively, it is also possible to calculate the average of a plurality of refraction angles φ1(x), φ2(x), . . . of each pixel 40 calculated by each imaging and to set $\phi_0/\phi_{avg}(x)$ as a correction coefficient of the pixel 40 using the average refraction angle $\phi_{avg}(x)$. Also in this case, since it is possible to reduce an influence of non-uniform refraction angles given to X-rays at the linear section 160A and the connecting section 160B, the correction coefficient of each pixel 40 can be precisely calculated.

Although the second transmission type grating 32 is used in the X-ray imaging systems 10 and 100 described above, the second transmission type grating 32 may be removed by using an X-ray image detector with a configuration disclosed in JP-A-2009-133823. This X-ray image detector is a direct conversion type X-ray image detector including a conversion layer, which converts X-rays into electric charges, and a charge collecting electrode, which collects electric charges converted in the conversion layer. The charge collecting electrode of each pixel is formed by arraying a plurality of linear electrode groups, in which linear electrodes arrayed at fixed periods are electrically connected to each other, such that the phases are different.

Figure 19:
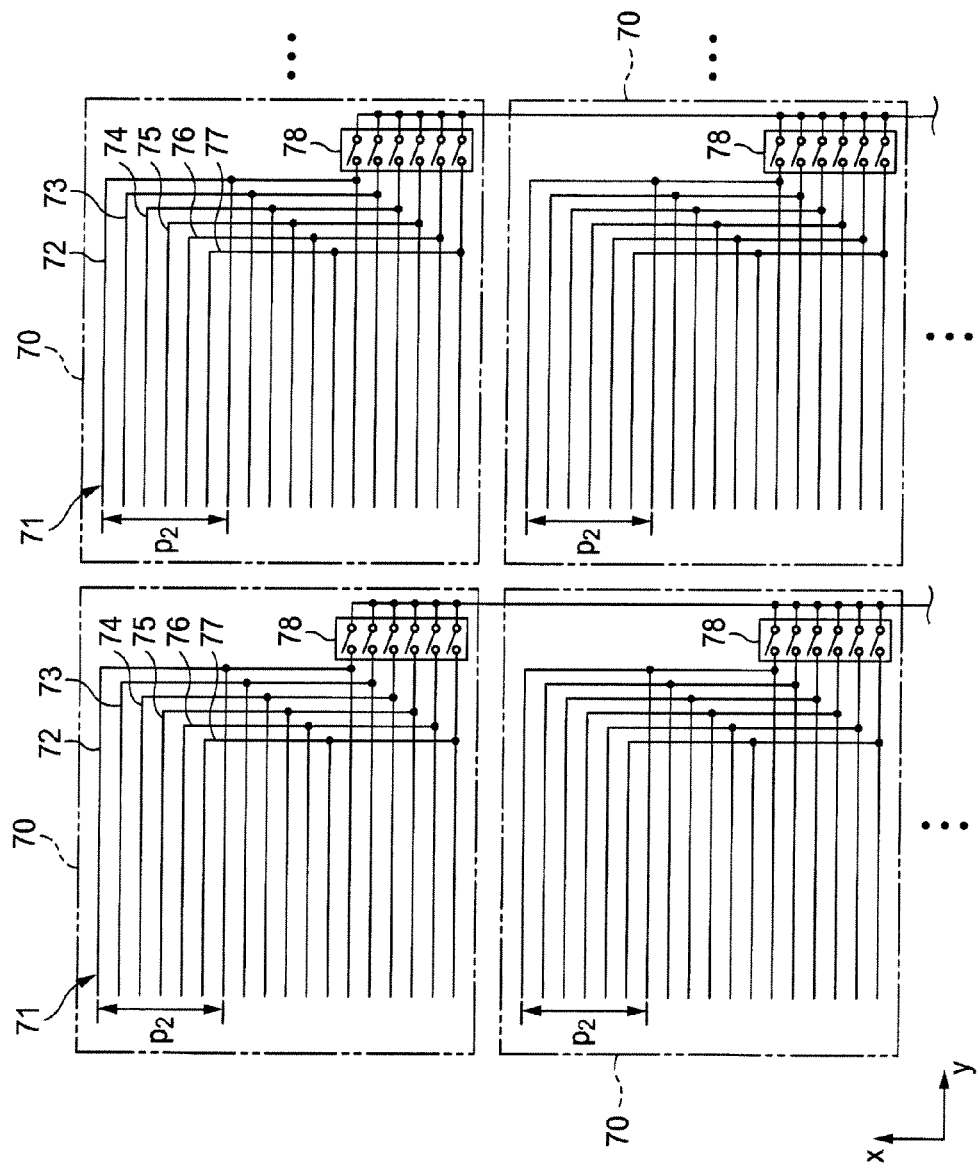
FIG. 19 is a schematic view showing the configuration of an example of a radiographic system for explaining an embodiment of the invention.

FIG. 19 illustrates the configuration of the above X-ray image detector (FPD). Pixels 70 are arrayed in a two-dimensional manner at fixed pitches along the x and y directions. A charge collecting electrode 71 for collecting electric charges converted by a conversion layer, which converts X-rays into electric charges, is formed in each pixel 70. The charge collecting electrode 71 is formed by first to sixth linear electrode groups 72 to 77, and the phase of an arrangement period of linear electrodes of each linear electrode group is shifted by π/3. Specifically, assuming that the phase of the first linear electrode group 72 is 0, the phase of the second linear electrode group 73 is π/3, the phase of the third linear electrode group 74 is 2π/3, the phase of the fourth linear electrode group 75 is π, the phase of the fifth linear electrode group 76 is 4π/3, and the phase of the sixth linear electrode group 77 is 5π/3. Electric charges of the pixel 70 in the y direction are stored through the linear electrode groups 72 to 77.

In addition, a switch group 78 for reading electric charges collected by the charge collecting electrode 71 is provided in each pixel 70. The switch group 78 is formed by a TFT switch provided in each of the first to sixth linear electrode groups 72 to 77. By controlling the switch group 78 to separately read electric charges collected by the first to sixth linear electrode groups 72 to 77, six kinds of fringe images with different phases can be acquired by one-time imaging. A phase contrast image can be generated on the basis of the six kinds of fringe images.

In the X-ray imaging systems 10 and 100 described above, the second transmission type grating 32 of the imaging unit 12 is not needed if the X-ray image detector with the above-described configuration is used instead of the FPD 30. As a result, a cost reduction and a further decrease in thickness can be realized. In addition, since a plurality of fringe images which is intensity-modulated with different phases can be acquired by one-time imaging in the present embodiment, physical scanning for fringe scanning is not necessary. Accordingly, the above-described scanning mechanism 33 can be removed. In addition, a charge collecting electrode with another configuration disclosed in JP-A-2009-133823 may be used instead of the charge collecting electrode 71.

Moreover, as another embodiment when the second transmission type grating 32 is not disposed, it is also possible to perform intensity modulation of a fringe image (G1 image) obtained by the X-ray image detector by performing sampling periodically while changing the phase by signal processing.

Figure 20:
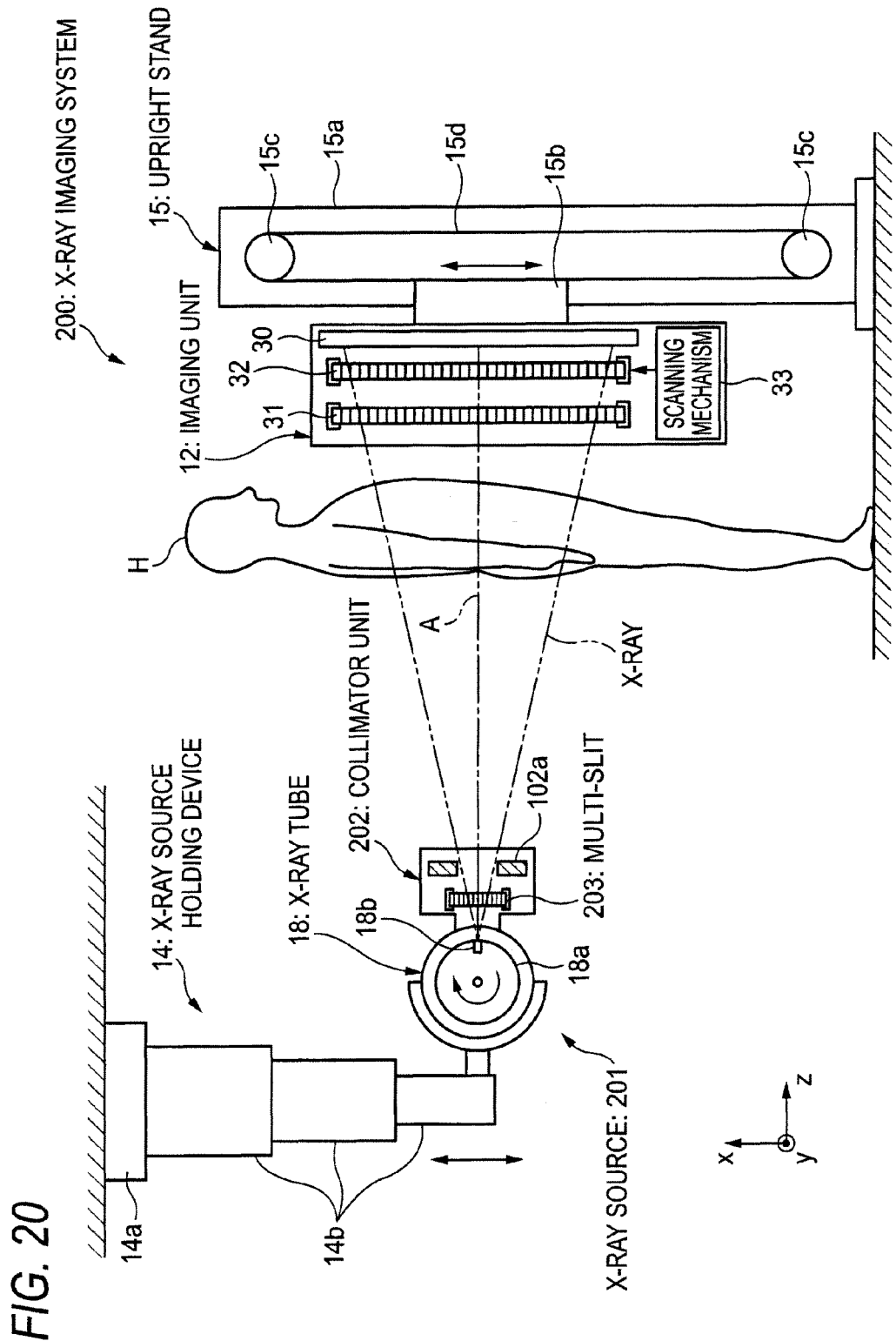
FIG. 20 is a schematic view showing the configuration of an example of a radiographic system for explaining an embodiment of the invention.
Figure 21:
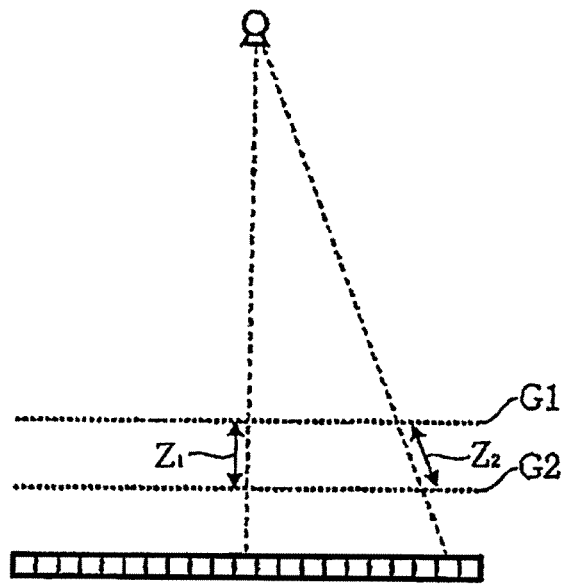
FIG. 21 is a schematic view showing an example of an error factor in phase imaging.
Figure 22:
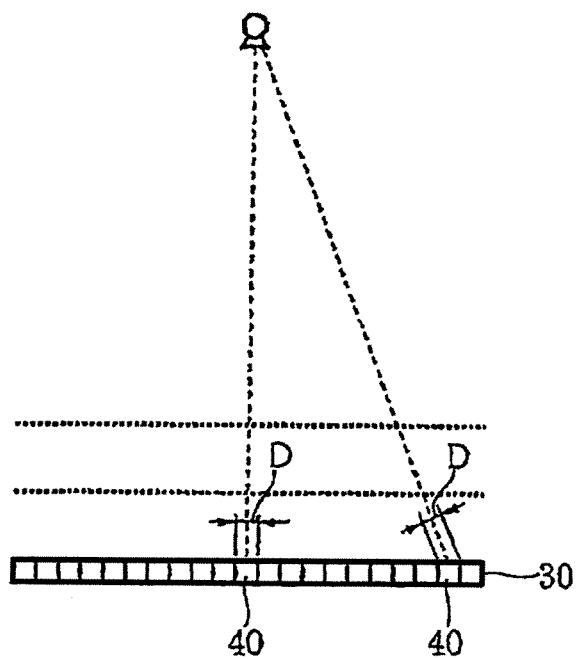
FIG. 22 is a schematic view showing an example of an error factor in phase imaging.

FIG. 20 shows another example of a radiographic system for explaining the embodiment of the invention.

An X-ray imaging system 200 shown in FIG. 20 is different from the above-described X-ray imaging system 10 in that a multi-slit 203 is provided in a collimator unit 202 of an X-ray source 201. Since the other configuration is the same as that of the X-ray imaging system 10, the explanation will be omitted.

In the X-ray imaging system 10 described above, if the distance from the X-ray source 11 to the FPD 30 is set as a distance (1 m to 2 m) which is set in an imaging room of a general hospital, the quality of a phase contrast image may be degraded due to an influence of blurring of the G1 image caused by the focal point size (generally, about 0.1 mm to 1 mm) of the X-ray focal point 18b. For this reason, reduction of the effective focal point size by providing a pinhole immediately after the X-ray focal point 18b may be considered. However, if the opening area of a pinhole is made small in order to reduce the effective focal point size, the X-ray intensity is reduced. In order to solve this problem, the multi-slit 203 is disposed immediately after the X-ray focal point 18b in the X-ray imaging system 200.

The multi-slit 203 is a transmission type grating (absorption type grating) with the same configuration as the first and second transmission type gratings 31 and 32 provided in the imaging unit 12, and a plurality of X-ray blocking sections extending in one direction (y direction) is periodically arrayed in the same direction (x direction) as the X-ray blocking sections 31b and 32b of the first and second transmission type gratings 31 and 32. The multi-slit 203 is provided to form a number of point light sources (distributed light sources) in the x direction by reducing the effective focal point size in the x direction by partially blocking the radiation emitted from the X-ray focal point 18b.

Assuming that the distance from the multi-slit 203 to the first transmission type grating 31 is $L_3$, it is necessary to set the grating pitch $p_3$ of the multi-slit 203 such that the following expression (27) is satisfied.

[Expression 27]

$$p_3 = \frac{L_3}{L_2} p_2 \quad (27)$$

Expression (27) is a geometric condition in which a projected image (G1 image) of X-rays, which are emitted from point light sources that are formed in a distributed way by the multi-slit 203, by the first transmission type grating 31 is the same (overlaps) at the position of the second transmission type grating 32.

In addition, since the position of the multi-slit 203 is substantially an X-ray focal position, the grating pitch $p_2$ of the second transmission type grating 32 are determined such that the relationships of the following expressions (28).

[Expression 28]

$$p_2 = \frac{L_3 + L_2}{L_3} p_1 \quad (28)$$

Thus, in the X-ray imaging system 200, the quality of a phase contrast image can be improved without reducing the X-ray intensity by superposition of the G1 image based on a plurality of point light sources formed by the multi-slit 203. The multi-slit 203 may also be applied to all of the X-ray imaging systems described above.

As described above, in this specification, there is disclosed a radiographic system which detects a radiation image transmitted through a subject with a radiation image detector and generates a phase contrast image of the subject. The radiographic system includes: a calculation section which calculates the distribution of refraction angles of radiation incident on the radiation image detector and generates a phase contrast image on the basis of the distribution of refraction angles; and a storage section which stores a correction coefficient of each pixel for making sensitivities of pixels equal, the correction coefficient being calculated on the basis of a refraction angle of radiation incident on each pixel of the radiation image detector, which is calculated by the calculation section by imaging a phantom that gives a known refraction angle to radiation transmitted through the phantom, and a refraction angle given to radiation by the phantom. The calculation section performs sensitivity correction on a refraction angle of radiation incident on each pixel of the radiation image detector, which is calculated by imaging the subject, using the correction coefficient of the pixel stored in the storage section and generates a phase contrast image of the subject on the basis of the distribution of corrected refraction angles.

Moreover, in this specification, there is disclosed a radiographic system in which the correction coefficient is a ratio of the refraction angle of radiation incident on each pixel of the radiation image detector, which is calculated by the calculation section by imaging the phantom, and the refraction angle given to radiation by the phantom.

Moreover, in this specification, there is disclosed a radiographic system further including: a first grating; and a grid pattern which substantially matches a periodic pattern of a radiation image generated by radiation transmitted through the first grating. The radiation image detector detects the radiation image masked with the grid pattern. The calculation section calculates the distribution of refraction angles of radiation incident on the radiation image detector from the image acquired by the radiation image detector.

Moreover, in this specification, there is disclosed a radiographic system in which the radiation image detector detects the radiation image masked with the grid pattern under a plurality of relative position relationships, in which phases of the grid pattern and the radiation image are different, and the refraction angle distribution is calculated by calculating the amount of phase shift of a signal of each pixel on the basis of a change in a signal value of each pixel in a plurality of images acquired by the radiation image detector.

Moreover, in this specification, there is disclosed a radiographic system in which the grid pattern is a second grating and a scanning means for moving at least one of the first and second gratings to put the second grating in the plurality of relative position relationships is further provided.

Moreover, in this specification, there is disclosed a radiographic system in which the radiation image detector has a conversion layer, which converts radiation into electric charges, and a charge collecting electrode, which collects electric charges converted in the conversion layer, for every pixel, the charge collecting electrode includes a plurality of linear electrode groups with a pattern which substantially matches the periodic pattern of the radiation image, and the plurality of linear electrode groups is arrayed to have different phases.

Moreover, in this specification, there is disclosed a radiographic system in which the grid pattern is the second grating and the radiation image masked with the second grating includes a moiré and the calculation section calculates the spatial frequency spectrum distribution by performing Fourier transform on the intensity distribution of the image, separates a spectrum corresponding to a basic frequency of the moiré from the calculated spatial frequency spectrum, and calculates the distribution of refraction angles by performing inverse Fourier transform on the separated spectrum.

Moreover, in this specification, there is disclosed a phantom used for sensitivity correction of the radiographic system described above. The phantom gives the same refraction angle to radiation transmitted through the phantom.

Moreover, in this specification, there is disclosed a phantom in which the phantom has an incidence surface, which is an arc with a focal point of the radiation source as the center on a cross section along a pitch direction of the periodic pattern of the radiation image, and a thickness of the phantom changes linearly around the focal point.

Moreover, in this specification, there is disclosed a phantom in which a thickness of the phantom changes linearly in a pitch direction of the periodic pattern of the radiation image.

Moreover, in this specification, there is disclosed a phantom used for sensitivity correction of the radiographic system described above. The phantom has an incidence surface, which is an arc with a focal point of the radiation source as the center on a cross section along a pitch direction of the periodic pattern of the radiation image, and a linear thickness change around the focal point is periodically repeated.

Moreover, in this specification, there is disclosed a phantom used for sensitivity correction of the radiographic system described above. A linear thickness change in a pitch direction of the periodic pattern of the radiation image is periodically repeated.

Moreover, in this specification, there is disclosed a radiographic method of detecting a radiation image transmitted through a subject with a radiation image detector and generating a phase contrast image of the subject. The radiographic method includes: calculating a correction coefficient of each pixel for making sensitivities of pixels equal on the basis of a refraction angle of radiation incident on each pixel of the radiation image detector, which is calculated by imaging a phantom that gives a known refraction angle to radiation transmitted through the phantom, and a refraction angle given to radiation by the phantom; and performing sensitivity correction on a refraction angle of radiation incident on each pixel of the radiation image detector, which is calculated by imaging the subject, using the correction coefficient of the pixel and generating a phase contrast image of the subject on the basis of the distribution of corrected refraction angles.

Moreover, in this specification, there is disclosed a radiographic method in which the correction coefficient is a ratio of the refraction angle of radiation incident on each pixel of the radiation image detector, which is calculated by the calculation section by imaging the phantom, and the refraction angle given to radiation by the phantom.

Moreover, in this specification, there is disclosed a radiographic method which further includes: generating a striped radiation image by making radiation transmitted through a first grating; masking the radiation image using a grid pattern which substantially matches a periodic pattern of the radiation image; detecting the radiation image masked with the grid pattern using the radiation image detector; and calculating the distribution of refraction angles of radiation incident on the radiation image detector on the basis of the image acquired by the radiation image detector.

Moreover, in this specification, there is disclosed a radiographic method in which the phantom gives the same refraction angle to radiation transmitted through the phantom.

Moreover, in this specification, there is disclosed a radiographic method in which the phantom has an incidence surface, which is an arc with a focal point of radiation as the center on a cross section along a pitch direction of a periodic pattern of the radiation image, and a linear thickness change around the focal point of radiation is periodically repeated and in which the phantom is imaged a plural number of times while rotating the phantom gradually by a predetermined angle around the focal point of radiation and the correction coefficient of each pixel is calculated on the basis of a plurality of refraction angles of radiation incident on each pixel of the radiation image detector, which is calculated by each imaging, and a refraction angle given to radiation by the phantom.

Moreover, in this specification, there is disclosed a radiographic method in which a linear thickness change in a pitch direction of a periodic pattern of the radiation image is periodically repeated and in which the phantom is imaged a plural number of times while rotating the phantom gradually by a predetermined distance in the pitch direction and the correction coefficient of each pixel is calculated on the basis of a plurality of refraction angles of radiation incident on each pixel of the radiation image detector, which is calculated by each imaging, and a refraction angle given to radiation by the phantom.

Moreover, in this specification, there is disclosed a computer readable medium storing a program causing a computer to execute a process for performing a radiographic method of detecting a radiation image transmitted through a subject with a radiation image detector and generating a phase contrast image of the subject, the radiographic method comprising: if a phantom that gives a known refraction angle to radiation transmitted through the phantom is imaged, (i) calculating a refraction angle of radiation incident on each pixel of the radiation image detector and (ii) calculating a correction coefficient of each pixel for making sensitivities of pixels equal on the basis of the calculated refraction angle and a refraction angle given to radiation by the phantom, and if a subject is imaged, (i) calculating a refraction angle of radiation incident on each pixel of the radiation image detector, (ii)

performing sensitivity correction on the calculated refraction angle of radiation incident on each pixel of the radiation image detector using the correction coefficient of the pixel, and (iii) generating a phase contrast image of the subject on the basis of the distribution of corrected refraction angles.

What is claimed is:

1. A radiographic system which detects a radiation image transmitted through a subject with a radiation image detector and generates a phase contrast image of the subject, comprising:
   a calculation section that calculates a distribution of refraction angles of radiation incident on the radiation image detector and generates the phase contrast image on the basis of the distribution of refraction angles; and
   a storage section that stores a correction coefficient of each pixel for making sensitivities of pixels equal, the correction coefficient being calculated on the basis of a refraction angle of radiation incident on each pixel of the radiation image detector, which is calculated by the calculation section by imaging a phantom that gives a known refraction angle to radiation transmitted through the phantom, and a refraction angle given to radiation by the phantom,
   wherein the calculation section performs sensitivity correction on a refraction angle of radiation incident on each pixel of the radiation image detector, which is calculated by imaging the subject, using the correction coefficient of the pixel stored in the storage section and generates the phase contrast image of the subject on the basis of the distribution of corrected refraction angles.

2. The radiographic system according to claim 1, wherein the correction coefficient is a ratio of the refraction angle of radiation incident on each pixel of the radiation image detector, which is calculated by the calculation section by imaging the phantom, and the refraction angle given to radiation by the phantom.

3. The radiographic system according to claim 1, further comprising:
   a first grating; and
   a grid pattern which substantially matches a periodic pattern of a radiation image generated by radiation transmitted through the first grating,
   wherein the radiation image detector detects the radiation image masked with the grid pattern, and
   the calculation section calculates the distribution of refraction angles of radiation incident on the radiation image detector from the image acquired by the radiation image detector.

4. The radiographic system according to claim 3, wherein the radiation image detector detects the radiation image masked with the grid pattern under a plurality of relative position relationships in which phases of the grid pattern and the radiation image are different, and
   the refraction angle distribution is calculated by calculating the amount of phase shift of a signal of each pixel on the basis of a change in a signal value of each pixel in a plurality of images acquired by the radiation image detector.

5. The radiographic system according to claim 4, wherein the grid pattern is a second grating, and
   a scanning means for moving at least one of the first and second gratings to put the second grating in the plurality of relative position relationships is further provided.

6. The radiographic system according to claim 4, wherein the radiation image detector has a conversion layer, which converts radiation into electric charges, and a charge collecting electrode, which collects electric charges converted in the conversion layer, for every pixel,
   the charge collecting electrode includes a plurality of linear electrode groups with a pattern which substantially matches the periodic pattern of the radiation image, and
   the plurality of linear electrode groups is arrayed to have different phases.

7. The radiographic system according to claim 3, wherein the grid pattern is the second grating, and the radiation image masked with the second grating includes a moiré, and
   the calculation section calculates the spatial frequency spectrum distribution by performing Fourier transform on the intensity distribution of the image, separates a spectrum corresponding to a basic frequency of the moiré from the calculated spatial frequency spectrum, and calculates the distribution of refraction angles by performing inverse Fourier transform on the separated spectrum.

8. A phantom used for sensitivity correction of the radiographic system according to claim 1,
   wherein the phantom gives the same refraction angle to radiation transmitted through the phantom.

9. The phantom according to claim 8,
   wherein the phantom has an incidence surface, which is an arc with a focal point of the radiation source as the center on a cross section along a pitch direction of the periodic pattern of the radiation image, and a thickness of the phantom changes linearly around the focal point.

10. The phantom according to claim 8,
    wherein a thickness of the phantom changes linearly in a pitch direction of the periodic pattern of the radiation image.

11. A phantom used for sensitivity correction of the radiographic system according to claim 1,
    wherein the phantom has an incidence surface, which is an arc with a focal point of the radiation source as the center on a cross section along a pitch direction of the periodic pattern of the radiation image, and a linear thickness change around the focal point is periodically repeated.

12. A phantom used for sensitivity correction of the radiographic system according to claim 1,
    wherein a linear thickness change in a pitch direction of the periodic pattern of the radiation image is periodically repeated.

13. A radiographic method of detecting a radiation image transmitted through a subject with a radiation image detector and generating a phase contrast image of the subject, comprising:
    calculating a correction coefficient of each pixel for making sensitivities of pixels equal on the basis of a refraction angle of radiation incident on each pixel of the radiation image detector, which is calculated by imaging a phantom that gives a known refraction angle to radiation transmitted through the phantom, and a refraction angle given to radiation by the phantom; and
    performing sensitivity correction on a refraction angle of radiation incident on each pixel of the radiation image detector, which is calculated by imaging the subject, using the correction coefficient of the pixel and generating a phase contrast image of the subject on the basis of the distribution of corrected refraction angles.

14. The radiographic method according to claim 13,
    wherein the correction coefficient is a ratio of the refraction angle of radiation incident on each pixel of the radiation image detector, which is calculated by imaging the phantom, and the refraction angle given to radiation by the phantom.

15. The radiographic method according to claim 13, further comprising:
   generating a striped radiation image by making radiation transmitted through a first grating;
   masking the radiation image using a grid pattern which substantially matches a periodic pattern of the radiation image;
   detecting the radiation image masked with the grid pattern using the radiation image detector; and
   calculating the distribution of refraction angles of radiation incident on the radiation image detector on the basis of the image acquired by the radiation image detector.

16. The radiographic method according to claim 13,
   wherein the phantom gives the same refraction angle to radiation transmitted through the phantom.

17. The radiographic method according to claim 13,
   wherein the phantom has an incidence surface, which is an arc with a focal point of radiation as the center on a cross section along a pitch direction of a periodic pattern of the radiation image, and a linear thickness change around the focal point of radiation is periodically repeated, and
   the phantom is imaged a plural number of times while rotating the phantom gradually by a predetermined angle around the focal point of radiation, and the correction coefficient of each pixel is calculated on the basis of a plurality of refraction angles of radiation incident on each pixel of the radiation image detector, which is calculated by each imaging, and a refraction angle given to radiation by the phantom.

18. The radiographic method according to claim 13,
   wherein a linear thickness change in a pitch direction of a periodic pattern of the radiation image is periodically repeated in the phantom, and
   the phantom is imaged a plural number of times while moving the phantom gradually by a predetermined distance in the pitch direction, and the correction coefficient of each pixel is calculated on the basis of a plurality of refraction angles of radiation incident on each pixel of the radiation image detector, which is calculated by each imaging, and a refraction angle given to radiation by the phantom.

19. A non-transitory computer readable medium storing a program causing a computer to execute a process for performing a radiographic method of detecting a radiation image transmitted through a subject with a radiation image detector and generating a phase contrast image of the subject, the radiographic method comprising:
   if a phantom that gives a known refraction angle to radiation transmitted through the phantom is imaged, (i) calculating a refraction angle of radiation incident on each pixel of the radiation image detector and (ii) calculating a correction coefficient of each pixel for making sensitivities of pixels equal on the basis of the calculated refraction angle and a refraction angle given to radiation by the phantom; and
   if a subject is imaged, (i) calculating a refraction angle of radiation incident on each pixel of the radiation image detector, (ii) performing sensitivity correction on the calculated refraction angle of radiation incident on each pixel of the radiation image detector using the correction coefficient of the pixel, and (iii) generating a phase contrast image of the subject on the basis of the distribution of corrected refraction angles.

* * * * *